United States Patent [19]

Mabuchi et al.

[11] 4,456,671

[45] Jun. 26, 1984

[54] ELECTROPHOTOGRAPHIC PHOTOSENSITIVE MEMBER HAVING A PHOTOSENSITIVE LAYER CONTAINING A HYDRAZONE COMPOUND

[75] Inventors: Minoru Mabuchi, Tokyo; Naoto Fujimura; Shozo Ishikawa, both of Yokohama; Yoshio Takasu, Tama; Kiyoshi Sakai, Mitaka; Masaki Kuribayashi, Tokyo, all of Japan

[73] Assignee: Canon Kabushiki Kaisha, Tokyo, Japan

[21] Appl. No.: 449,417

[22] Filed: Dec. 13, 1982

[30] Foreign Application Priority Data

| Dec. 23, 1981 | [JP] | Japan | 56-208912 |
|---|---|---|---|
| Dec. 23, 1981 | [JP] | Japan | 56-208913 |
| Dec. 23, 1981 | [JP] | Japan | 56-208914 |
| Dec. 24, 1981 | [JP] | Japan | 56-215483 |
| Dec. 24, 1981 | [JP] | Japan | 56-215484 |
| Dec. 25, 1981 | [JP] | Japan | 56-214699 |
| Dec. 25, 1981 | [JP] | Japan | 56-214700 |
| Dec. 25, 1981 | [JP] | Japan | 56-214701 |

[51] Int. Cl.$^3$ .......................... G03G 5/06; G03G 5/14
[52] U.S. Cl. ...................................... 430/58; 430/79; 430/60
[58] Field of Search ...................... 430/70, 73, 75, 79, 430/82, 58, 60

[56] References Cited

U.S. PATENT DOCUMENTS

| 3,180,729 | 4/1965 | Klupfel et al. |
|---|---|---|
| 3,378,554 | 4/1968 | Pushchel et al. |
| 3,484,237 | 12/1969 | Shattuck et al. |
| 3,684,502 | 8/1972 | Gramza et al. |
| 3,775,105 | 11/1973 | Kukla |
| 3,775,108 | 11/1973 | Arai et al. |
| 3,824,099 | 7/1974 | Champ et al. |
| 3,837,851 | 9/1974 | Shattuck et al. |
| 3,870,516 | 3/1975 | Smith et al. |
| 3,871,882 | 3/1975 | Wiedemann |
| 3,884,691 | 5/1975 | Rochlitz |
| 3,887,935 | 4/1975 | Regensburger et al. |
| 3,894,868 | 7/1975 | Regensburger et al. |
| 4,024,125 | 5/1977 | Kunstmann et al. |
| 4,122,113 | 10/1978 | Purner |
| 4,150,987 | 4/1979 | Anderson et al. |
| 4,251,614 | 2/1981 | Sasaki et al. |
| 4,256,821 | 3/1981 | Enomoto et al. |
| 4,260,672 | 4/1981 | Sasaki |
| 4,265,991 | 5/1981 | Hirai et al. |
| 4,272,598 | 6/1981 | Sasaki et al. |
| 4,278,747 | 7/1981 | Murayama et al. |
| 4,279,981 | 7/1981 | Ohta et al. |
| 4,297,426 | 10/1981 | Sakai et al. |

FOREIGN PATENT DOCUMENTS

| 0013172 | 7/1980 | European Pat. Off. |
|---|---|---|
| 2302522 | 8/1981 | Fed. Rep. of Germany |
| 43-1619768 | 7/1968 | Japan |
| 48-71236 | 9/1973 | Japan |
| 51-94829 | 8/1976 | Japan |
| 54-112637 | 9/1979 | Japan |
| 54-119925 | 9/1979 | Japan |
| 54-121742 | 9/1979 | Japan |
| 55-17105 | 2/1980 | Japan |
| 55-108667 | 8/1980 | Japan |
| 930988 | 7/1963 | United Kingdom |
| 1030024 | 5/1966 | United Kingdom |
| 1296390 | 11/1972 | United Kingdom |
| 1370197 | 10/1976 | United Kingdom |
| 1453024 | 10/1976 | United Kingdom |
| 1465141 | 2/1977 | United Kingdom |
| 1465142 | 2/1977 | United Kingdom |
| 2001769A | 2/1979 | United Kingdom |
| 2018446A | 10/1979 | United Kingdom |
| 2034493A | 6/1980 | United Kingdom |
| 2052082A | 1/1981 | United Kingdom |
| 2055803A | 3/1981 | United Kingdom |
| 2034494A | 6/1982 | United Kingdom |

Primary Examiner—John E. Kittle
Assistant Examiner—John L. Goodrow
Attorney, Agent, or Firm—Fitzpatrick, Cella, Harper & Scinto

[57] ABSTRACT

An electrophotographic photosensitive member comprises a layer containing a binder and at least one hydrazone compound represented by the following formula (1), (2), (3), (4), or (5):

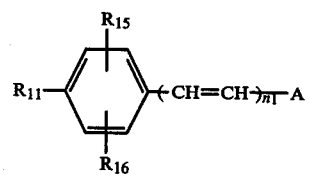

Formula (1)

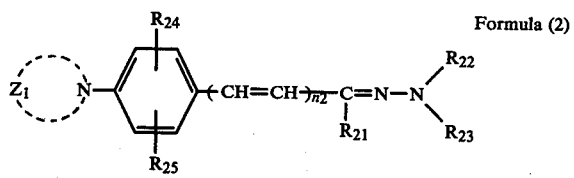

Formula (2)

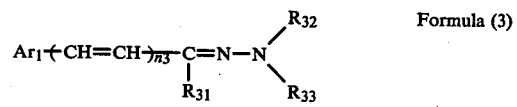

Formula (3)

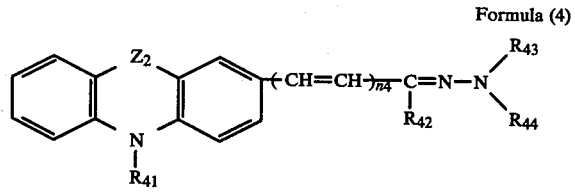

Formula (4)

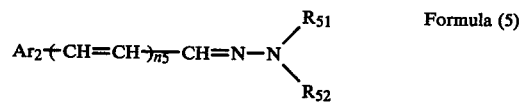

Formula (5)

26 Claims, No Drawings

ELECTROPHOTOGRAPHIC PHOTOSENSITIVE MEMBER HAVING A PHOTOSENSITIVE LAYER CONTAINING A HYDRAZONE COMPOUND

BACKGROUND OF THE INVENTION

1. Field of the Invention

This invention relates to electrophotographic photosensitive members and more particularly to an electrophotographic photosensitive member having a photosensitive layer containing a specific hydrazone compound which is a novel organic photoconductive substance.

2. Description of the Prior Art

Inorganic photoconductive materials such as selenium, cadmium sulfide, zinc oxide, etc. have so far been known as photoconductive materials used for electrophotographic photosensitive members. Contrary to their many advantages, as chargeability to a suitable potential in the dark, high retention of charge in the dark, and fast dissipation of charge on exposure to light, these photoconductive materials have various disadvantages, for instance, as follows: selenium type photoconductive materials readily crystallize under the influence of such factors as heat, moisture, dust, pressure, and the like; in particular, when the surrounding temperature exceeds 40° C., their crystallization becomes remarkable, resulting in deterioration of their chargeability or white spots in images formed therewith. Selenium type or cadmium type photoconductive materials lack stable sensitivity and durability for use under high humidity conditions. Zinc oxide type photoconductive materials, which require sensitization with a sensitizing pigment including Rose Bengal as a typical example, cannot give stable images over a long period of time because the sensitizing pigment tends to be degraded by corona charging and faded by light exposure.

On the other hand, there have been offered various kinds of organic photoconductive polymers including polyvinylcarbazole and the like. These polymers, however, have been hardly put to practical use until now, in spite of their better film-forming property and their lightweight, as compared with the foregoing inorganic photoconductive materials. The reason for this is that their film-forming property is still unsatisfactory and inferior to the inorganic photoconductive materials in sensitivity, durability, and stability to changes in environmental conditions.

Further, low-molecular organic photoconductive materials have been offered including hydrazone compounds and the like disclosed in U.S. Pat. Nos. 4,150,987 and 4,278,747, German Patent Offen No. 2939483, British Patent Laid-Open No. 2034493, and European Patent Laid-Open No. 13172. Although the insufficient film-forming property which has been a problem in the field of organic photoconductive polymers can be overcome by using these low-molecular organic photoconductive materials with a properly selected binder, their initial potential on charging is low and dark decay thereof is significant. In addition, they are inferior in the ability to restore original charge bearing characteristics when they are put again in the dark after being retained in the light for a given time (this restoring power is referred to as "photomemory property"). These drawbacks cause various problems.

SUMMARY OF THE INVENTION

An object of this invention is to provide a novel electrophotographic photosensitive member free from the foregoing defects or disadvantages.

Another object of this invention is to provide a novel organic photoconductive material.

A further object of this invention is to provide an electrophotographic photosensitive member improved in initial peak potential and dark potential retentiveness (dark decay).

Still another object of this invention is to provide an electrophotographic photosensitive member improved in its photomemory property.

A further object of this invention is to provide a novel charge-transporting compound suitable for use in a photosensitive layer of laminated structure comprising a charge generation layer and a charge transport layer.

According to the present invention, there is provided an electrophotographic photosensitive member comprising a layer containing a binder and at least one hydrazone compound represented by the following formula (1), (2), (3), (4), (5):

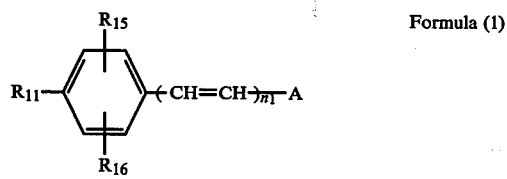

Formula (1)

In Formula (1); $R_{11}$ represents alkoxy or di-substituted amino; $R_{15}$ and $R_{16}$ represent hydrogen, halogen, or an organic monovalent residue; $n_1$ is 0 or 1; and A represents

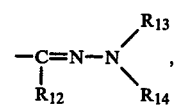

wherein $R_{12}$, $R_{13}$, and $R_{14}$ represent alkyl, aryl, or aralkyl, substituted or unsubstituted, with the proviso that,
when $R_{12}$ is alkyl, $R_{13}$ represents aryl and $R_{14}$ represents alkyl, aryl, or aralkyl,
when $R_{12}$ is aryl, $R_{13}$ represents aralkyl and $R_{14}$ represents aryl, and
when $R_{12}$ is aralkyl, $R_{13}$ and $R_{14}$ represent alkyl, aryl, or aralkyl.

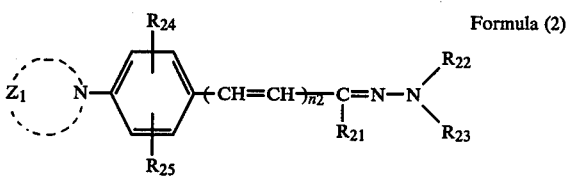

Formula (2)

In Formula (2); $Z_1$ represents a residue necessary to complete a cyclic amino group; $R_{21}$, $R_{22}$, and $R_{23}$ represent alkyl, aryl, or aralkyl, substituted or unsubstituted; $R_{24}$ and $R_{25}$ represent hydrogen, halogen, or an organic monovalent residue; and $n_2$ is 0 or 1.

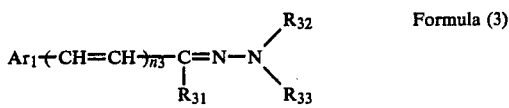

Formula (3)

In Formula (3); $Ar_1$ represents a substituted or unsubstituted aromatic polycyclic residue; $R_{31}$, $R_{32}$, and $R_{33}$ represent alkyl, aryl, or aralkyl, substituted or unsubstituted; and $n_3$ is 0 or 1.

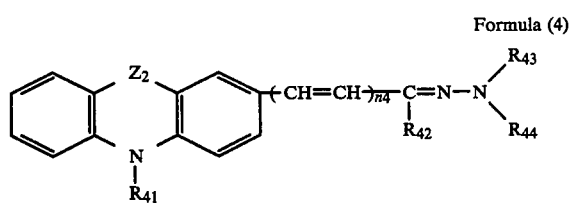

Formula (4)

In Formula (4); $Z_2$ represents oxygen, sulfur, or $-CH_2-$; $R_{41}$ represents alkyl or aralkyl, substituted or unsubstituted; $R_{42}$, $R_{43}$, and $R_{44}$ represent alkyl, aryl, or aralkyl, substituted or unsubstituted; and $n_4$ is 0 or 1.

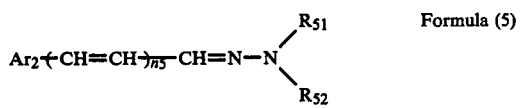

Formula (5)

In Formula (5); $Ar_2$ represents a substituted or unsubstituted aromatic polycyclic residue or a phenyl substituted at least by piperidino or morpholine; $R_{51}$ represents substituted or unsubstituted naphthyl; $R_{52}$ represents alkyl, aryl, or aralkyl, substituted or unsubstituted; and $n_5$ is 0 or 1.

DETAILED DESCRIPTION OF THE PREFRRED EMBODIMENTS OF THE INVENTION

The hydrazone compounds contained in the electrophotographic photosensitive member of this invention are represented by the following formulas (1)–(5):

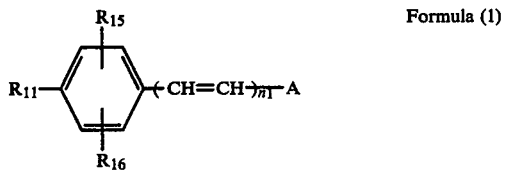

Formula (1)

In Formula (1); $R_{11}$ represents di-substituted amino (e.g. dialkylamino such as dimethylamino, diethylamino, diporpylamino, dibutylamino, diamylamino, or the like; diaralkylamino such as dibenzylamino, diphenethylamino, or the like; or diarylamino such as diphenylamino, ditolylamino, dixylylamino, or the like) or alkoxy (e.g. methoxy, ethoxy, propoxy, butoxy, or the like);

$R_{15}$ and $R_{16}$ represent hydrogen, halogen (e.g. chlorine, bromine, or the like), or an organic monovalent residue (e.g. alkyl such as methyl, ethyl, propyl, butyl, or the like; alkoxy such as methoxy, ethoxy, propoxy, butoxy, or the like; di-substituted amino such as dimethylamino, diethylamino, dipropylamino, dibutylamino, dibenzylamino, diphenylamino, or the like; hydroxyl; cyano; or acyl such as acetyl, propionyl, benzoyl, toluoyl, or the like) n is 0 or 1:

A represents $-C=N-N\begin{smallmatrix}R_{13}\\ \\ R_{12} \quad R_{14}\end{smallmatrix}$ wherein $R_{12}$ represents alkyl (e.g. methyl, ethyl, propyl, butyl, amyl, hexyl, octyl, or the like), substituted alkyl (e.g. 2-chloroethyl, 3-chloropropyl, 2-hydroxyethyl, 3-hydroxypropyl, 2-methoxyethyl, 3-methoxypropyl, 4-methoxybutyl, 2-ethoxyethyl, 3-ethoxypropyl, 4-ethoxybutyl, or the like), aryl (e.g. phenyl, naphthyl, or the like), substituted aryl (e.g. tolyl, xylyl, biphenyl, dimethylaminophenyl, diethylaminophenyl, dipropylaminophenyl, dibutylaminophenyl, dibenzylaminophenyl, diphenethylaminophenyl, diphenylaminophenyl, methoxyphenyl, ethoxyphenyl, propoxyphenyl, butoxyphenyl, acetylphenyl, chlorophenyl, bromophenyl, cyanophenyl, hydroxyphenyl, or the like), aralkyl (e.g. benzyl, phenethyl, naphthylmethyl, or the like), or substituted aralkyl (e.g. methoxybenzyl, ethoxybenzyl, propoxybenzyl, methylbenzyl, ethylbenzyl, chlorobenzyl, hydroxybenzyl, or the like), $R_{13}$ and $R_{14}$ represent alkyl (e.g. methyl, ethyl, propyl, butyl, amyl, hexyl, octyl, or the like), substituted alkyl (e.g. 2-chloroethyl, 3-chloropropyl, 2-hydroxyethyl, 3-hydroxypropyl, 2-methoxyethyl, 3-methoxypropyl, 4-methoxybutyl, 2-ethoxyethyl, 3-ethoxypropyl, 4-ethoxybutyl, or the like), aralkyl (e.g. benzyl, phenethyl, naphthylmethyl, or the like), substituted aralkyl (e.g. methoxybenzyl, dimethoxybenzyl, propoxybenzyl, methylbenzyl, ethylbenzyl, chlorobenzyl, dichlorobenzyl, dimethylaminobenzyl, diethylaminobenzyl, hydroxybenzyl, or the like), aryl (e.g. phenyl, naphthyl, or the like), or substituted aryl (e.g. tolyl, xylyl, ethylphenyl, diethylphenyl, methoxyphenyl, ethoxyphenyl, dimethylaminophenyl, diethylaminophenyl, dipropylaminophenyl, chlorophenyl, dichlorophenyl, methoxynapthyl, ethoxynaphthyl, or the like).

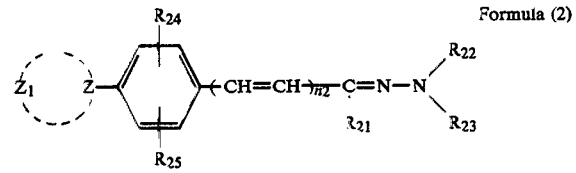

Formula (2)

In Formula (2); $Z_1$ represents a residue necessary to complete a cyclic amino group (e.g. piperidino, pyrrolidinyl, morpholine, or the like);

$R_{21}$, $R_{22}$, and $R_{23}$ represent alkyl (e.g. methyl, ethyl, propyl, butyl, amyl, hexyl, octyl, or the like), substituted alkyl (e.g. 2-chloroethyl, 3-chloropropyl, 2-hydroxyethyl, 3-hydroxypropyl, 2-methoxyethyl, 3-methoxypropyl, 4-methoxybutyl, 2-ethoxyethyl, 3-ethoxypropyl, 4-ethoxybutyl, or the like), aralkyl (e.g. benzyl, phenethyl, naphthylmethyl, or the like), substituted aralkyl (e.g. methoxybenzyl, dimethoxybenzyl, methylbenzyl, ethylbenzyl, chlorobenzyl, dichlorobenzyl, dimethylaminobenzyl, diethylaminobenzyl, or the like), aryl (e.g. phenyl, naphthyl, or the like), or substituted aryl (tolyl, xylyl, ethylphenyl, diethylphenyl, methoxyphenyl, ethoxyphenyl, dimethylaminophenyl, diethylaminophenyl, dipropylaminophenyl, chlorophenyl, dichlorophenyl, or the like);

$R_{24}$ and $R_{25}$ represent hydrogen, halogen (e.g. chlorine, bromine, or the like), or an organic monovalent residue (e.g. alkyl such as methyl, ethyl, propyl, butyl, or the like; alkoxy such as methoxy, ethoxy, propoxy, butoxy, or the like; di-substituted amino such as dimethylamino, diethylamino, dipropylamino, dibutylamino, dibenzylamino, diphenylamino, or the like; hydroxyl; cyano; or acyl such as acetyl, propionyl, benzoyl, toluoyl, or the like); and n is 0 or 1.

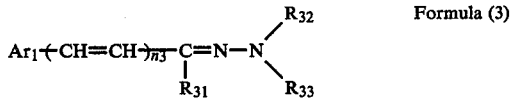

Formula (3)

In Formula (3); $Ar_1$ represents an aromatic polycyclic hydrocarbon residue (e.g. naphthyl, anthryl, pyrenyl, or the like); these aromatic rings may or may not be substituted by halogen (e.g. chlorine, bromine, or the like), alkyl (e.g. methyl, ethyl, propyl, butyl, or the like), alkoxy (e.g. methoxy, ethoxy, propoxy, butoxy, or the like), or di-substituted amino (e.g. dimethylamino, diethylamino, dipropylamino, dibutylamino, dibenzylamino, diphenylamino, or the like); $R_{31}$, $R_{32}$, and $R_{33}$ represent alkyl (e.g. methyl, ethyl, propyl, butyl, amyl, hexyl, octyl, or the like), substituted alkyl (e.g. 2-chloroethyl, 3-chloropropyl, 2-hydroxyethyl, 3-hydroxypropyl, 2-methoxyethyl, 3-methoxypropyl, 4-methoxybutyl, 2-ethoxyethyl, 3-ethoxypropyl, 4-ethoxybutyl, or the like), aralkyl (e.g. benzyl, phenethyl, naphthylmethyl, or the like), substituted aralkyl (e.g. methoxybenzyl, dimethoxybenzyl, methylbenzyl, ethylbenzyl, chlorobenzyl, dichlorobenzyl, dimethylaminobenzyl, diethylaminobenzyl, or the like), aryl (e.g. phenyl, naphthyl, or the like), or substituted aryl (e.g. tolyl, xylyl, ethylphenyl, diethylphenyl, methoxyphenyl, ethoxyphenyl, dimethylaminophenyl, diethylaminophenyl, dipropylaminophenyl, chlorophenyl, dichlorophenyl, or the like); and $n_3$ is 0 or 1.

Formula (4)

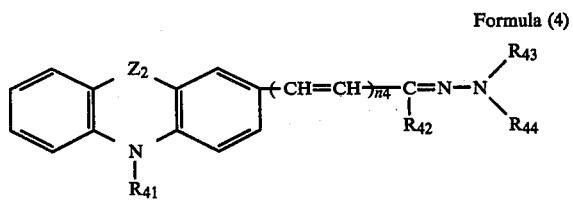

In Formula (4); $Z_2$ represents oxygen, sulfur, or —$CH_2$—; $R_{41}$ represents alkyl (e.g. methyl, ethyl, propyl, butyl, amyl, or the like), substituted alkyl (e.g. 2-hydroxyethyl, 3-hydroxypropyl, 2-chloroethyl, 3-chloropropyl, 2-methoxyethyl, 3-methoxypropyl, 4-methoxybutyl, 3-ethoxypropyl, 4-ethoxybutyl, or the like), aralkyl (e.g. benzyl, phenethyl, naphthylmethyl, or the like), or substituted aralkyl (e.g. methoxybenzyl, ethoxybenzyl, methylbenzyl, ethylbenzyl, chlorobenzyl, hydroxybenzyl, cyanobenzyl, or the like); $R_{42}$, $R_{43}$, and $R_{44}$ represent alkyl (e.g. methyl, ethyl, propyl, butyl, amyl, hexyl, octyl, or the like) substituted alkyl (e.g. 2-chloroethyl, 3-chloropropyl, 2-hydroxyethyl, 3-hydroxypropyl, 2-methoxyethyl, 3-methoxypropyl, 4-methoxybutyl, 2-ethoxyethyl, 3-ethoxypropyl, 4-ethoxybutyl, or the like), aralkyl (e.g. benzyl, phenethyl, naphthylmethyl, or the like), substituted aralkyl (e.g. methoxybenzyl, dimethoxybenzyl, methylbenzyl, ethylbenzyl, chlorobenzyl, dichlorobenzyl, dimethylaminobenzyl, diethylaminobenzyl, or the like), aryl (e.g. phenyl, naphthyl, or the like), or substituted aryl (e.g. tolyl, xylyl, ethylphenyl, diethylphenyl, methoxyphenyl, ethoxyphenyl, dimethylaminophenyl, diethylaminophenyl, dipropylaminophenyl, chlorophenyl, dichlorophenyl, or the like); and $n_4$ is 0 or 1.

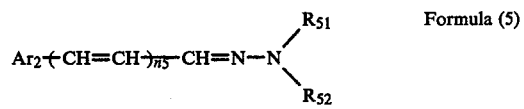

Formula (5)

In Formula (5); $Ar_2$ represents an aromiatic polycyclic hydrocarbon residue (e.g. naphthyl, anthryl, pyrenyl, or the like) these aromatic rings may or may not be substituted by halogen (e.g. chlorine, bromine, or the like), alkyl (e.g. methyl, ethyl, propyl, butyl, or the like), alkoxy (e.g. methoxy, ethoxy, propoxy, butoxy, or the like), or di-substituted amino (e.g. dimethylamino, diethylamino, dipropylamino, dibutylamino, dibenzylamino, diphenylamino, or the like); $Ar_2$ represents alternatively a phenyl substituted at least by piperidino or morpholino; additional substituents on the phenyl may include halogens (e.g. chlorine bromine, and the like), alkyls (e.g. methyl, ethyl, propyl, butyl, and the like), alkoxy (e.g. methoxy, ethoxy, propoxy, butoxy, and the like), di-substituted aminos (e.g. dimethylamino, diethylamino, dipropylamino, dibutylamino, dibenzylamino, diphenylamino, and the like), hydroxyl, cyano, and acyls (e.g. acetyl, propionyl, benzoyl, toluoyl, and the like);

$R_{51}$ represents substituted or unsubstituted naphthyl; the naphthyl can have substituents such as alkyls (e.g. methyl, ethyl, propyl, butyl, and the like), alkoxys (e.g. methoxy, ethoxy, propoxy, butoxy, and the like), acyls (e.g. acetyl, propionyl, butyryl, benzoyl, and the like), halogens (e.g. chlorine, bromine, and the like), hydroxyl, cyano, and the like;

$R_{52}$ represents alkyl (e.g. methyl, ethyl, propyl, butyl, amyl, hexyl, octyl, or the like), substituted alkyl (e.g. 2-chloroethyl, 3-chloropropyl, 2-hydroxyethyl, 3-hydroxypropyl, 2-methoxyethyl, 3-methoxypropyl, 4-methoxybutyl, 2-ethoxyethyl, 3-ethoxypropyl, 4-ethoxybutyl, or the like), aralkyl (e.g. benzyl, phenethyl, naphthylmethyl, or the like), substituted aralkyl (e.g. methoxybenzyl, dimethoxybenzyl, methylbenzyl, ethylbenzyl, chlorobenzyl, dichlorobenzyl, dimethylaminobenzyl, diethylaminobenzyl, or the like), aryl (e.g. phenyl, napthyl, or the like), or substituted aryl (e.g. tolyl, xylyl, ethylphenyl, diethylphenyl, methoxyphenyl, ethoxyphenyl, dimethylaminophenyl, diethylaminophenyl, dipropylaminophenyl, chlorophenyl, dichlorophenyl, or the like); and $n_5$ is 0 or 1.

Typical examples of hydrazone compounds represented by Formula (1), (2), (3), (4), or (5) are given below.

Hydrazone compounds represented by Formula (1)

(1)

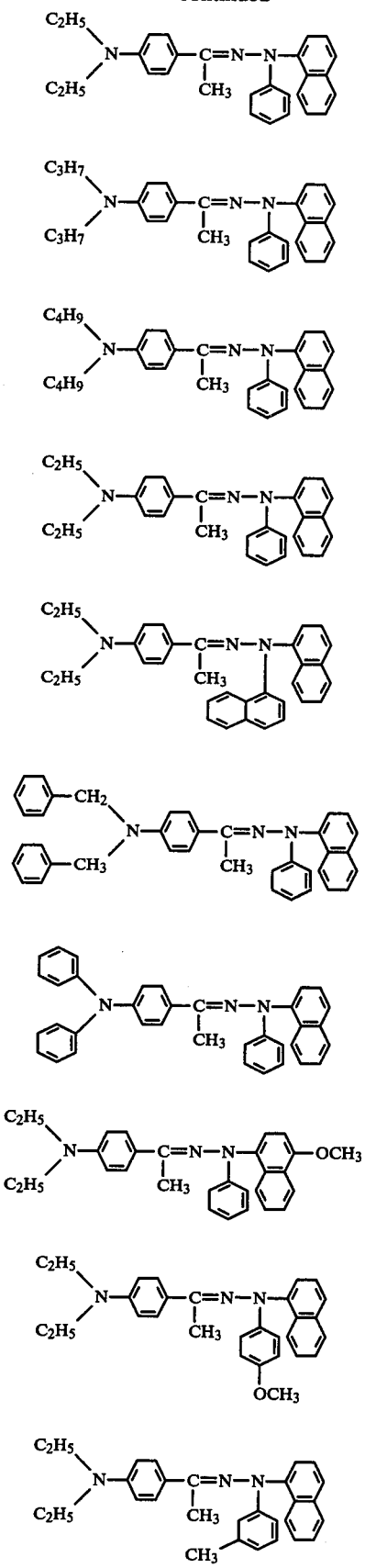
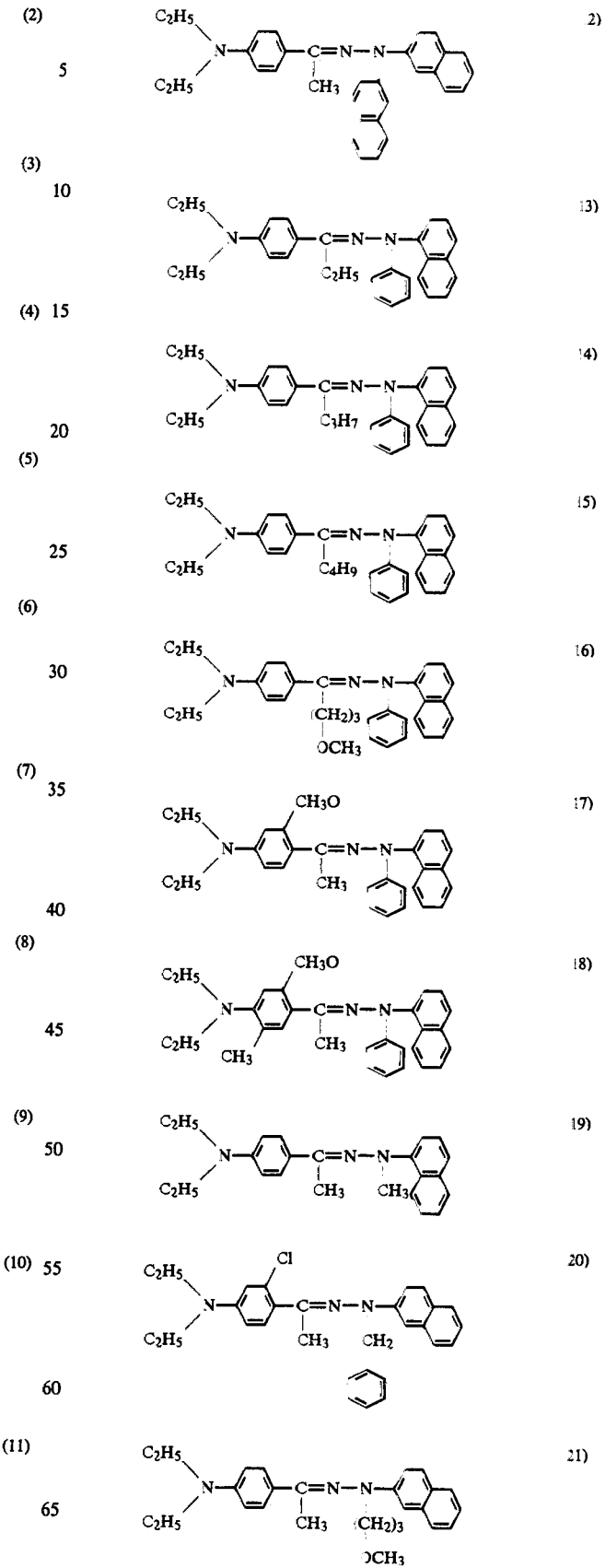

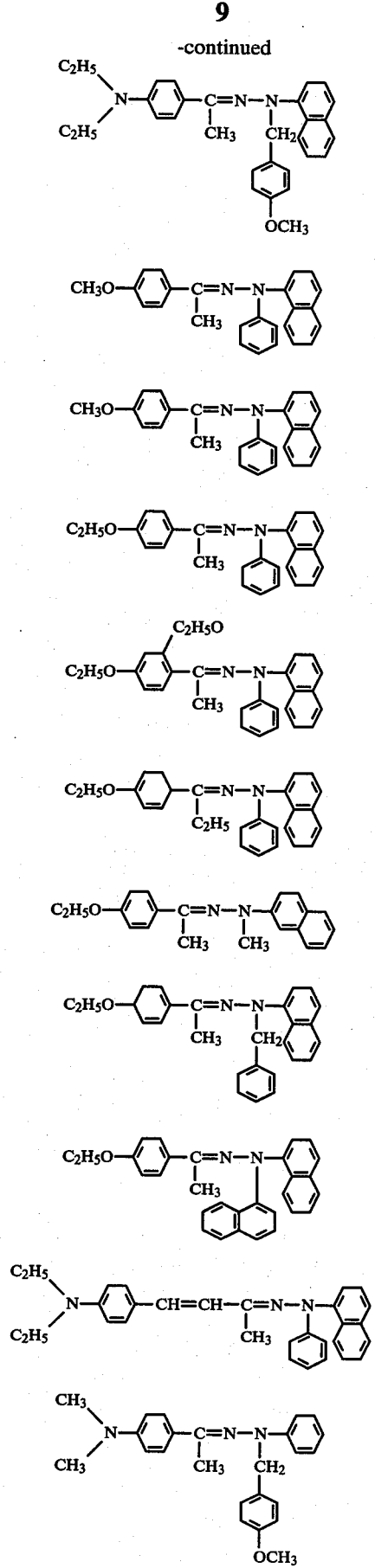
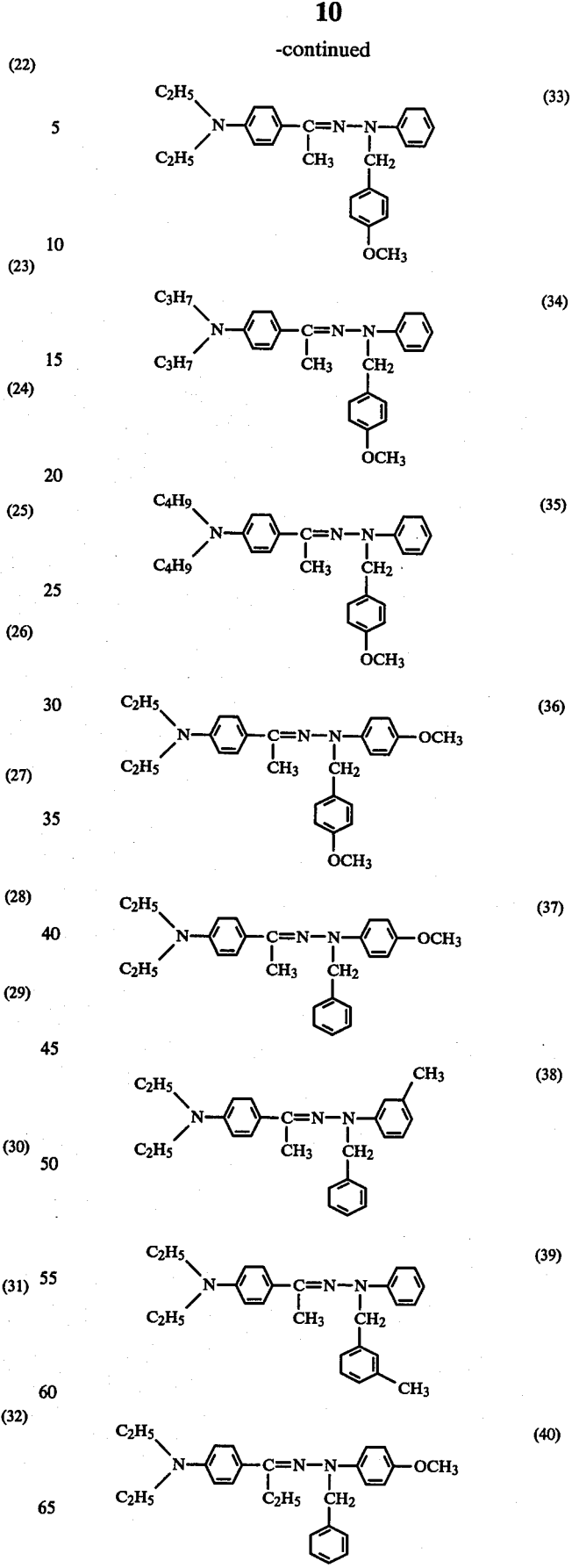

-continued
(41) 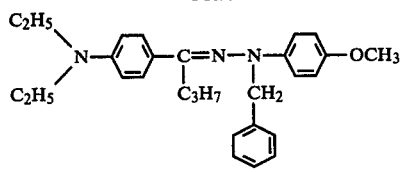
(42) 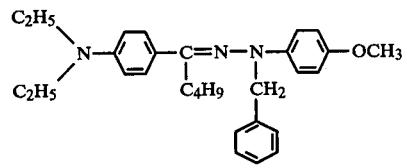
(43) 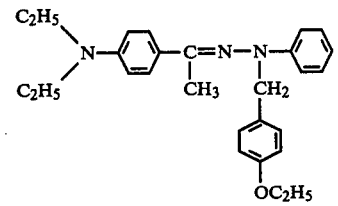
(44) 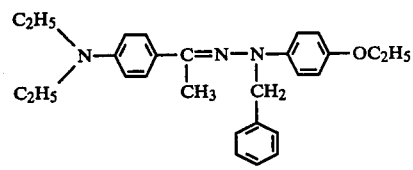
(45) 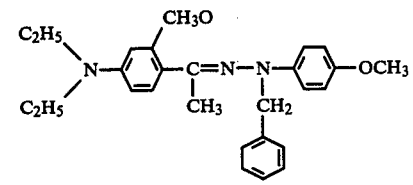
(46) 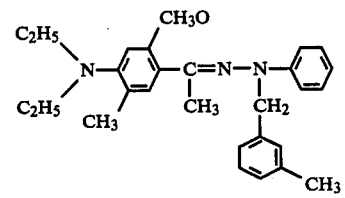
(47) 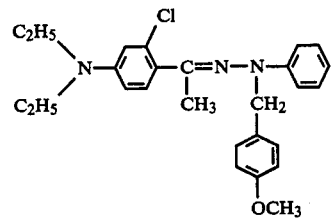
(48) 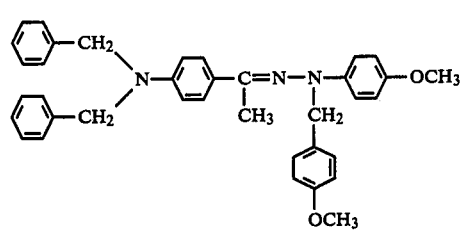
-continued
(49) 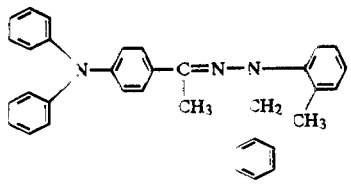
(50) 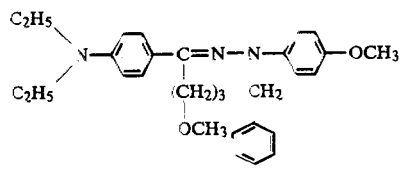
(51) 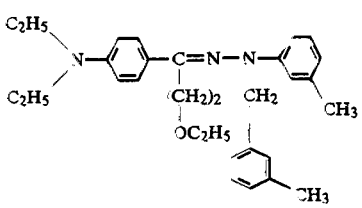
(52) 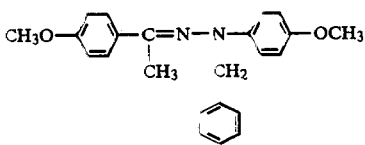
(53) 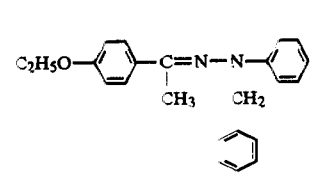
(54) 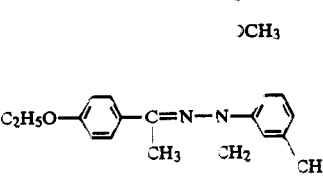
(55) 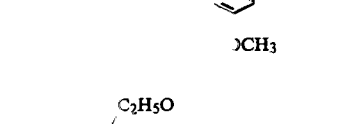
(56) 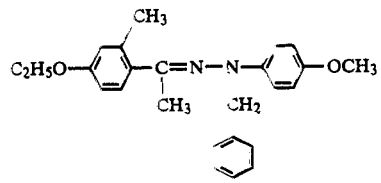

-continued
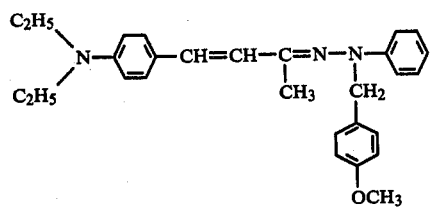 (57)
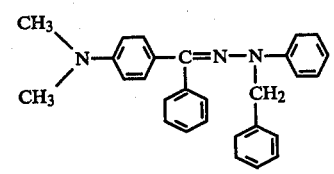 (58)
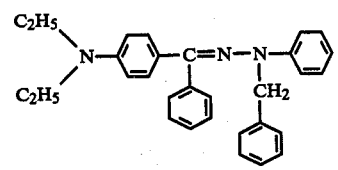 (59)
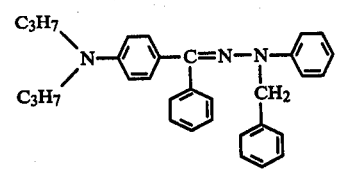 (60)
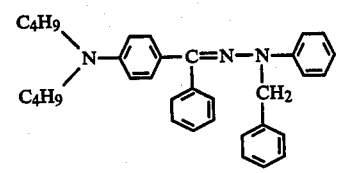 (61)
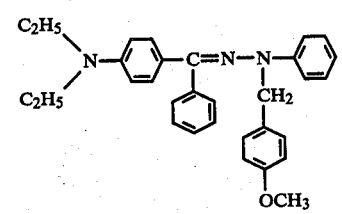 (62)
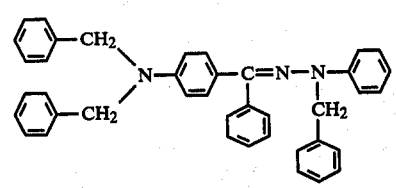 (63)
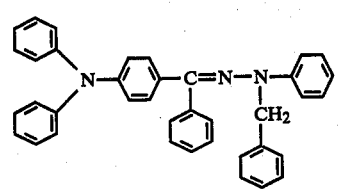 (64)
-continued
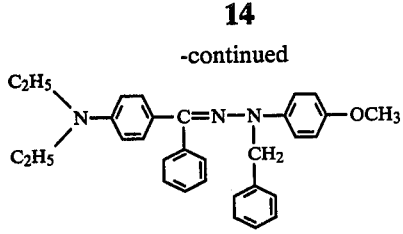 (65)
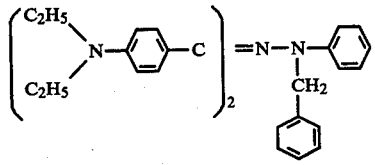 (66)
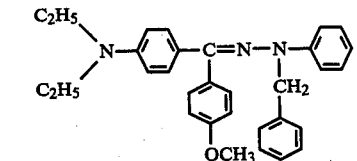 (67)
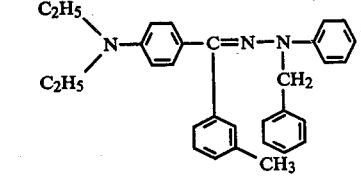 (68)
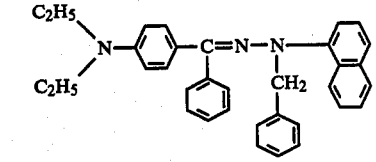 (69)
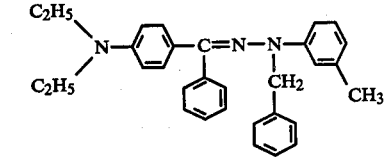 (70)
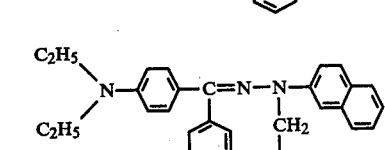 (71)
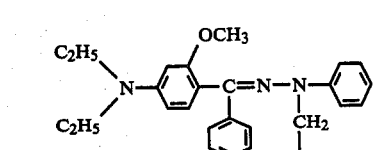 (72)
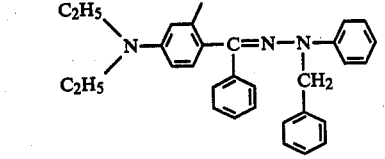 (73)

-continued
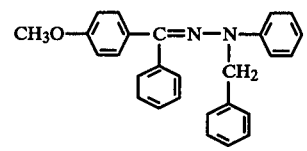 (74)
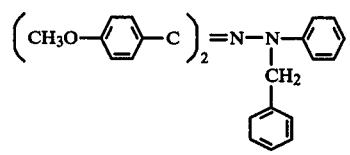 (75)
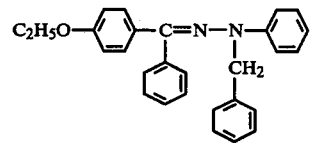 (76)
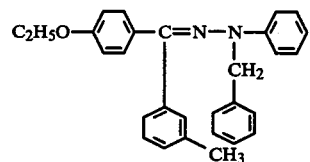 (77)
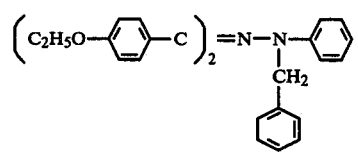 (78)
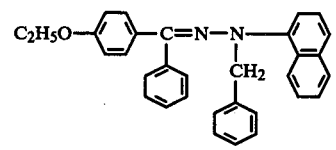 (79)
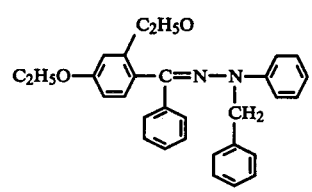 (80)
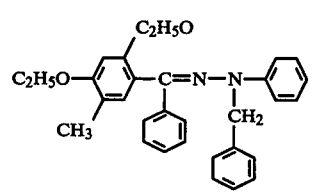 (81)
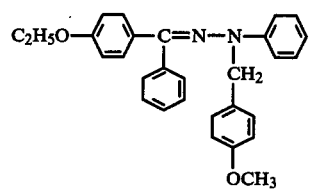 (82)

-continued
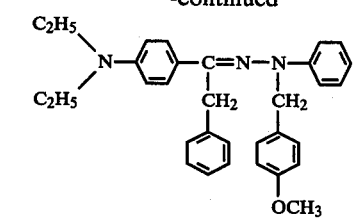 (92)
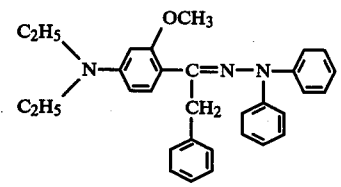 (93)
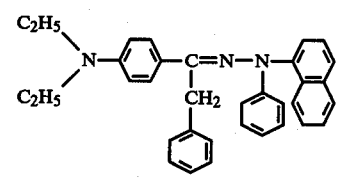 (94)
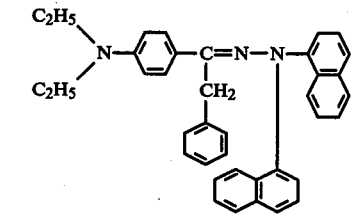 (95)
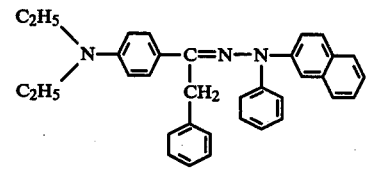 (96)
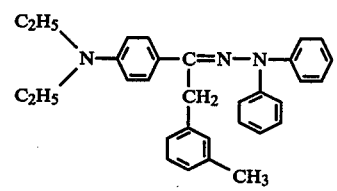 (97)
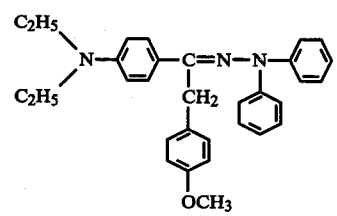 (98)
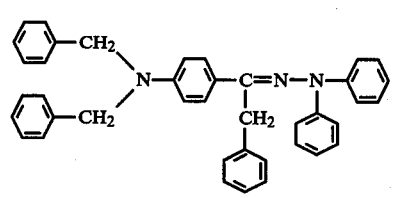 (99)
-continued
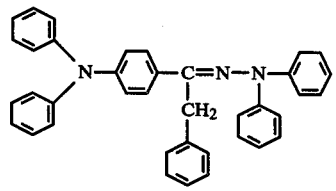 (100)
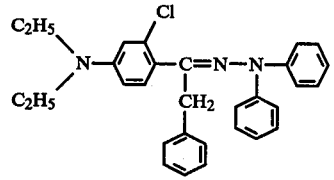 (101)
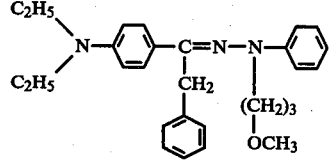 (102)
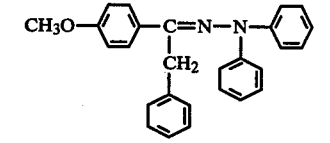 (103)
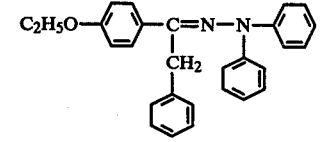 (104)
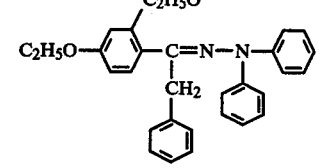 (105)
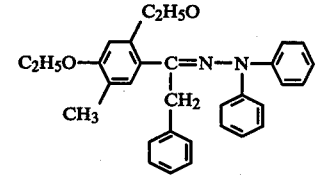 (106)
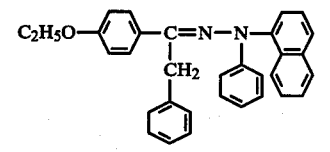 (107)
(108)

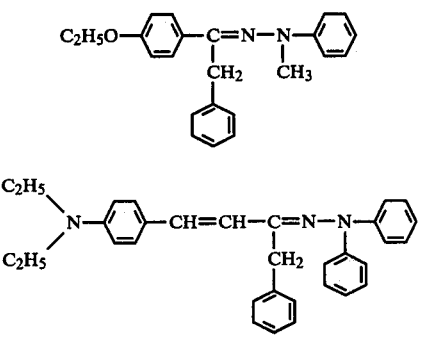 (109)
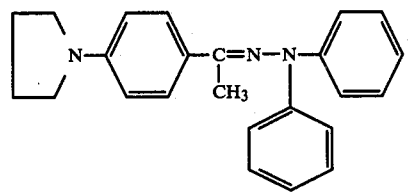 (110)
Hydrazone compounds represented by Formula (2)
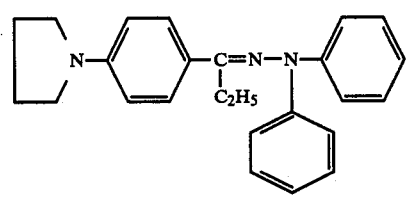 (111)
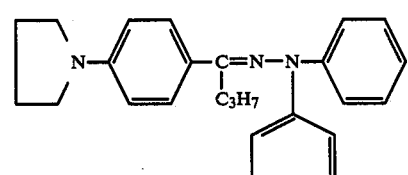 (112)
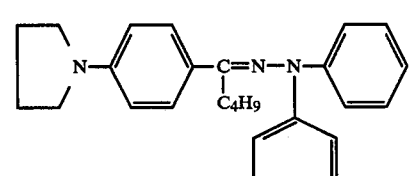 (113)
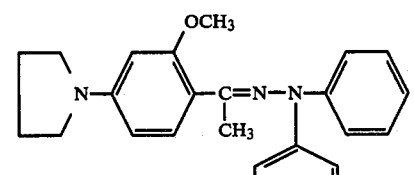 (114)
 (115)
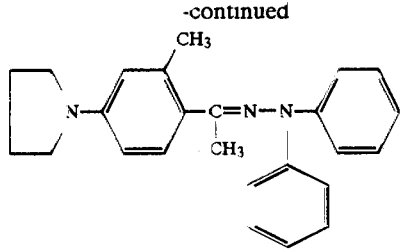 (116)
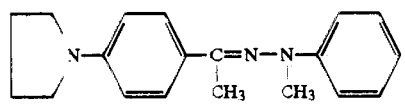 (117)
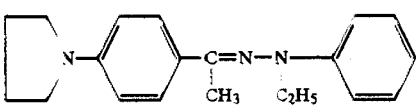 (118)
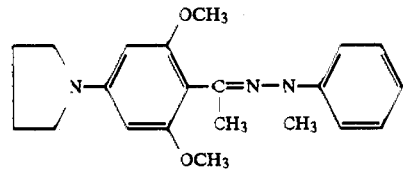 (119)
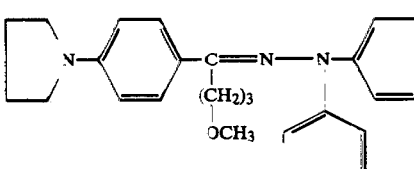 (120)
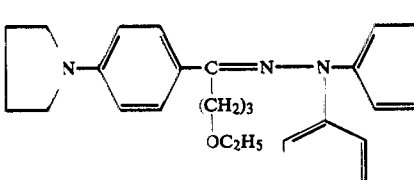 (121)
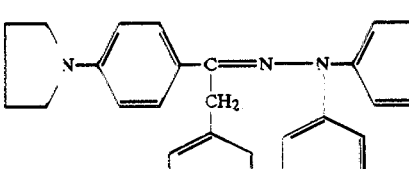 (122)
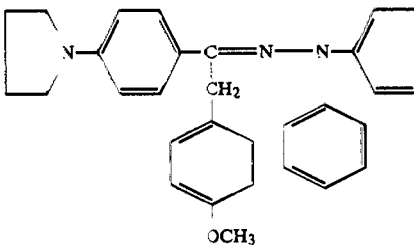 (123)

-continued
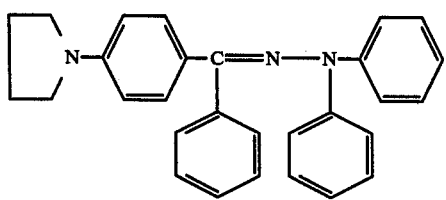 (124)
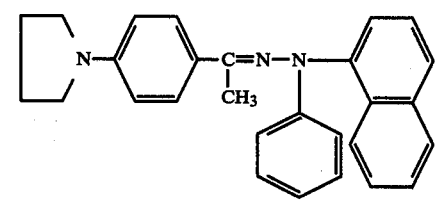 (125)
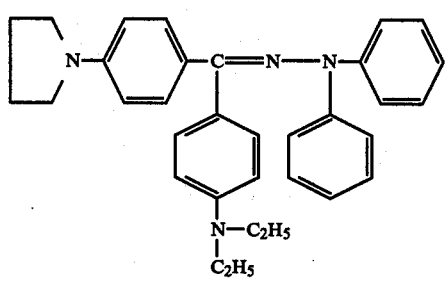 (126)
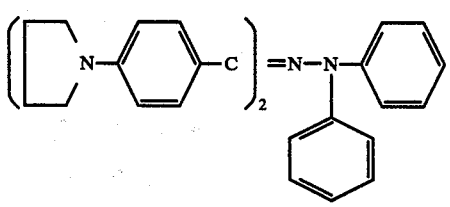 (127)
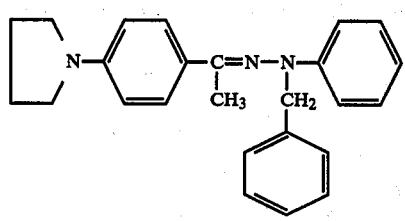 (128)
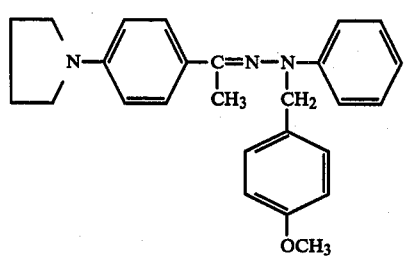 (129)
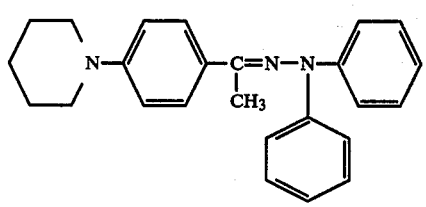 (130)
-continued
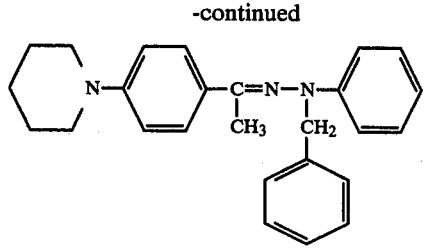 (131)
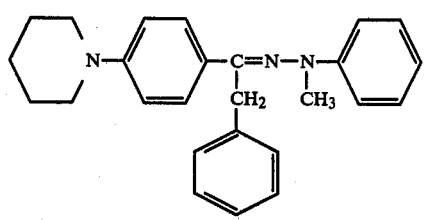 (132)
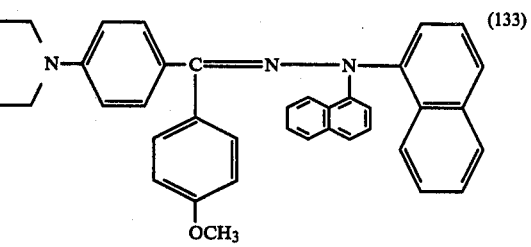 (133)
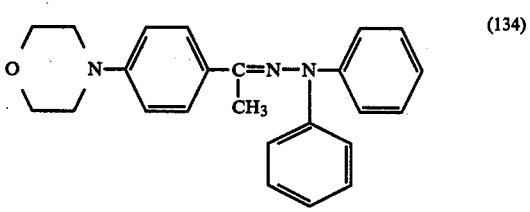 (134)
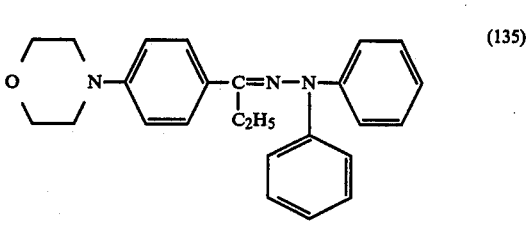 (135)
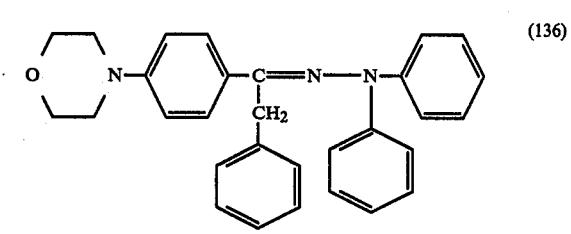 (136)
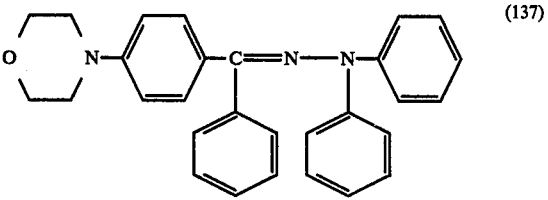 (137)

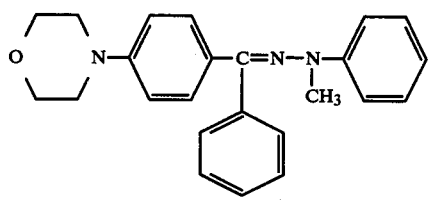 (138)
 (139)
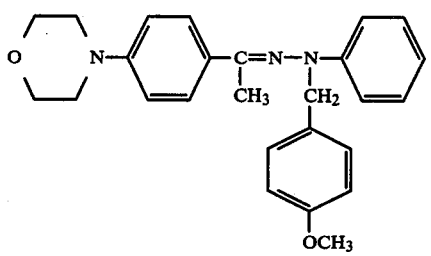 (140)
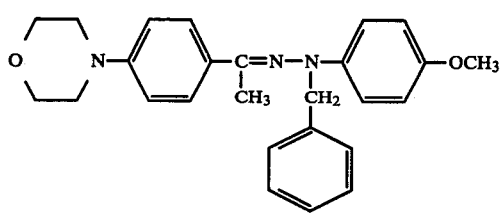 (141)
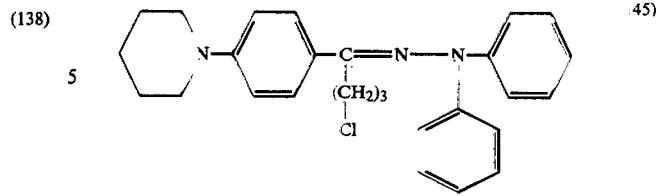 (142)
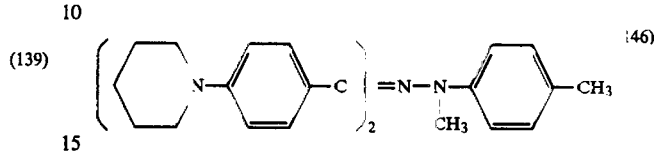 (143)
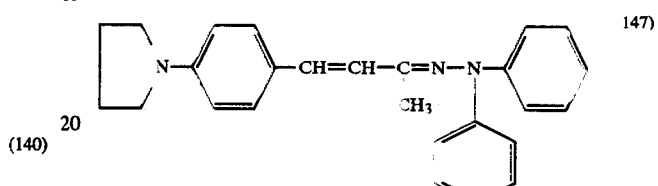 (144)
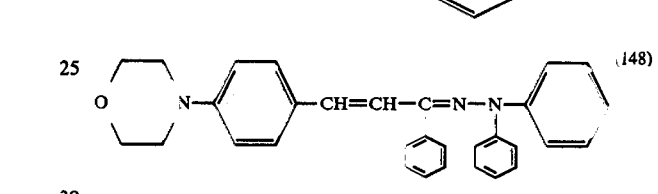 (145)
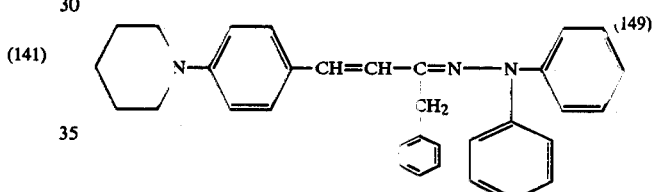 (146)
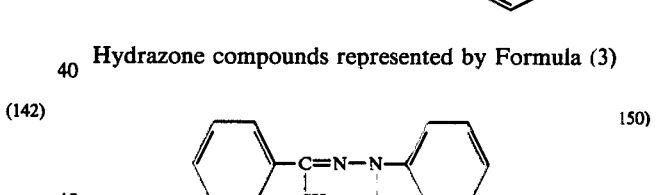 (147)
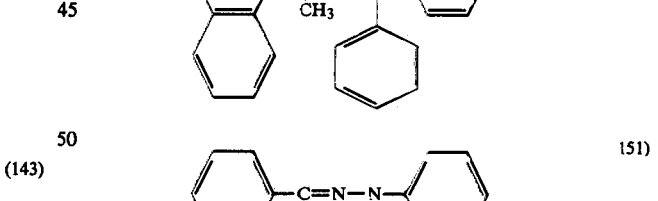 (148)
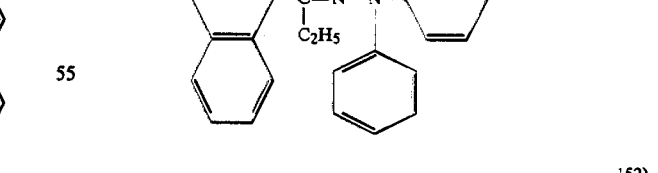 (149)
Hydrazone compounds represented by Formula (3)
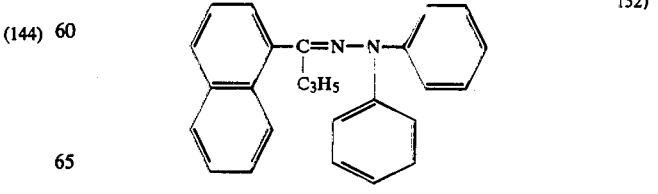 (150)
 (151)
 (152)

-continued
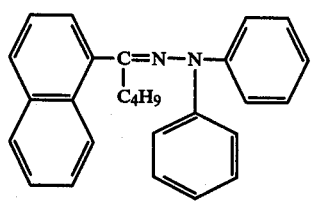 (153)
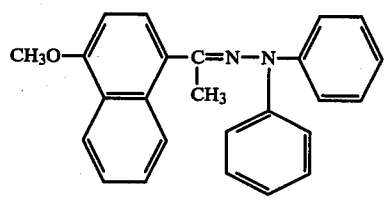 (154)
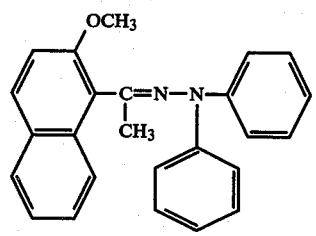 (155)
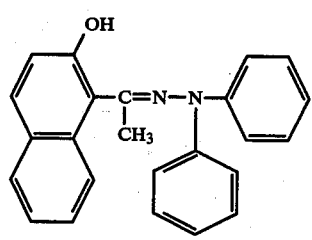 (156)
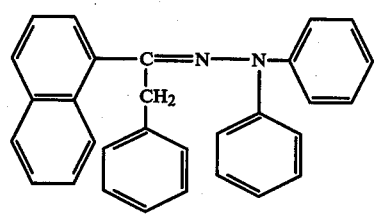 (157)
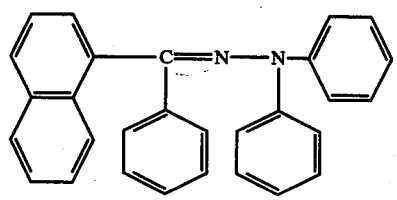 (158)
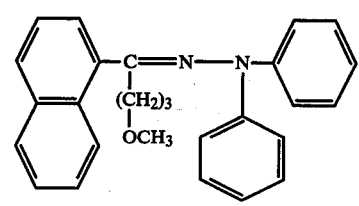 (159)
-continued
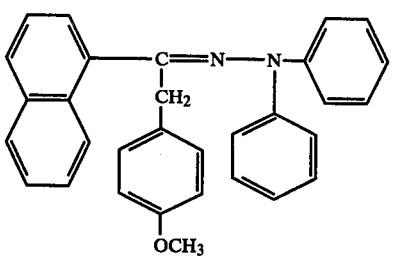 (160)
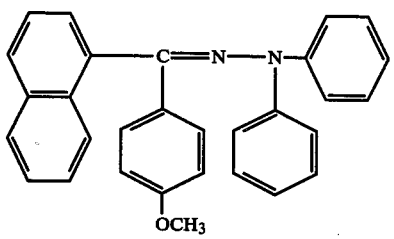 (161)
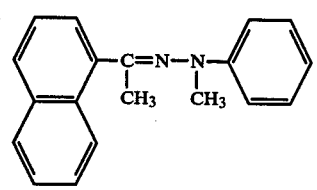 (162)
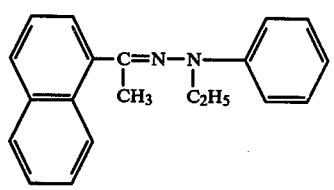 (163)
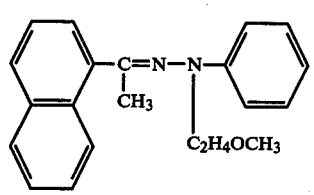 (164)
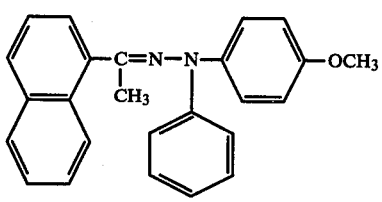 (165)
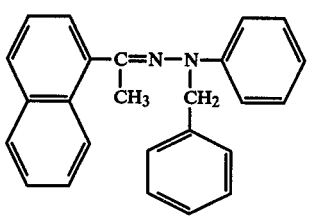 (166)

(178) 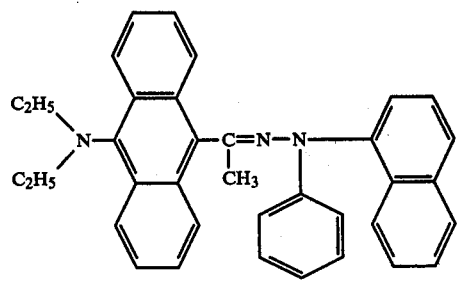
(179) 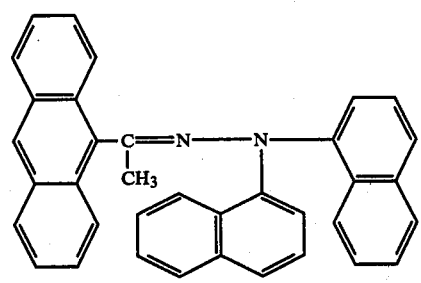
(180) 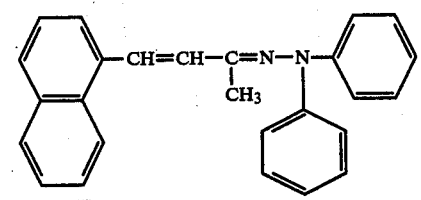
(181) 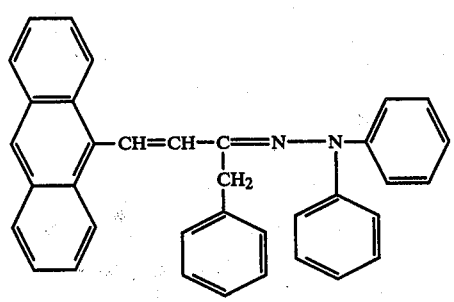
Hydrazone compounds represented by Formula (4)
(182) 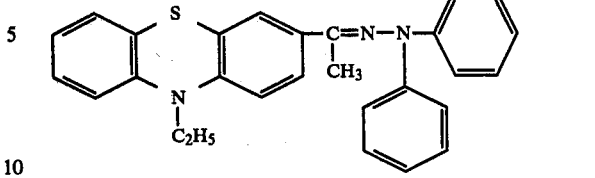
(183) 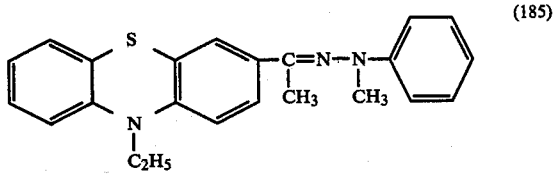
(184) 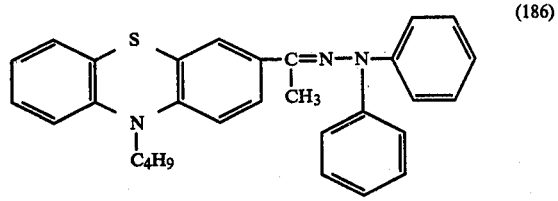
(185) 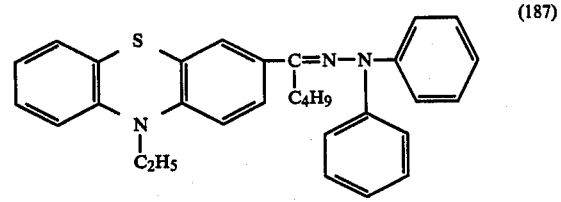
(186) 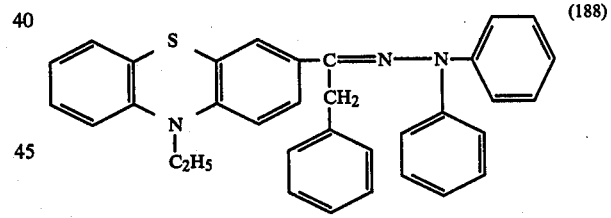
(187) 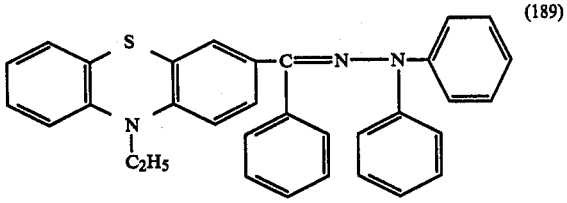
(188) 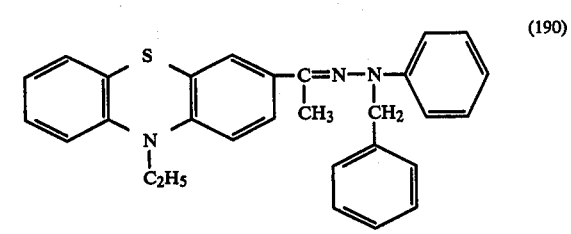
(189)
(190)

-continued
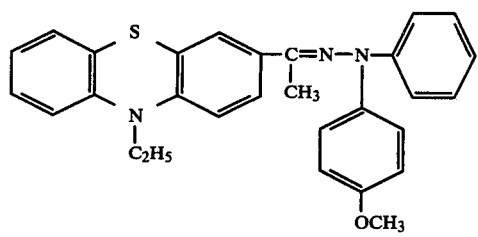 (191)
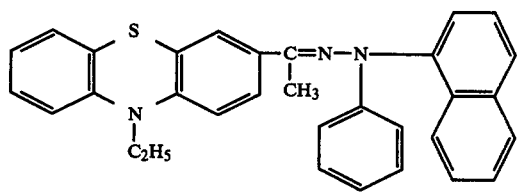 (192)
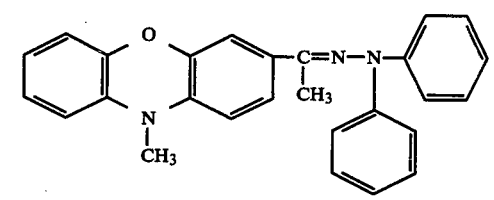 (193)
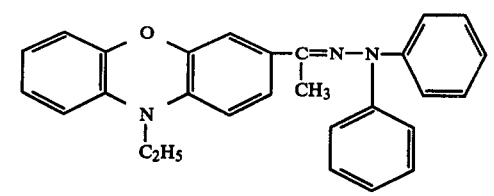 (194)
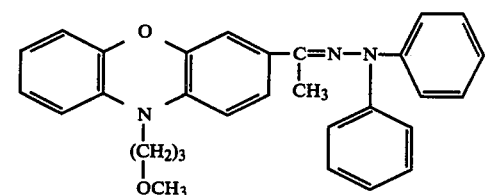 (195)
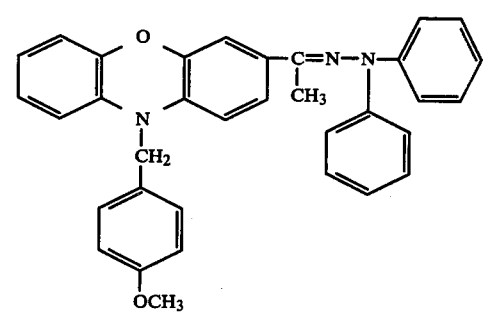 (196)
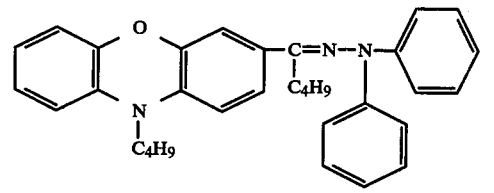 (197)
-continued
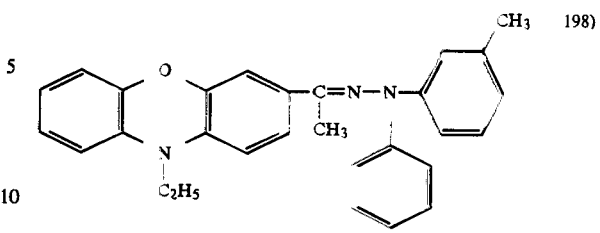 (198)
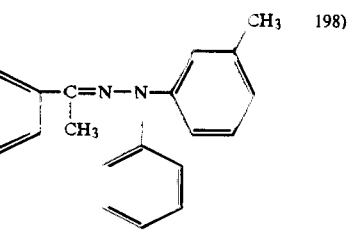 (199)
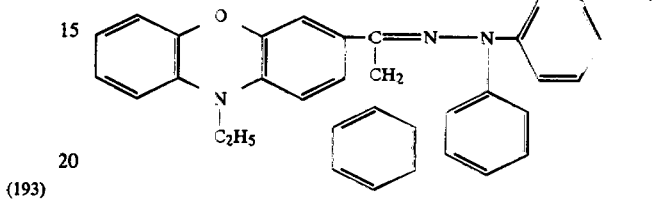 (200)
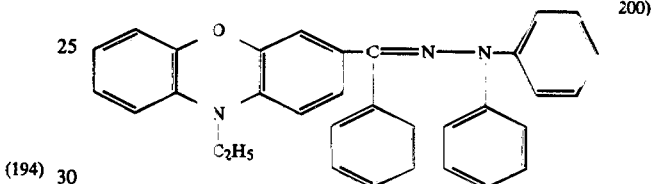 (201)
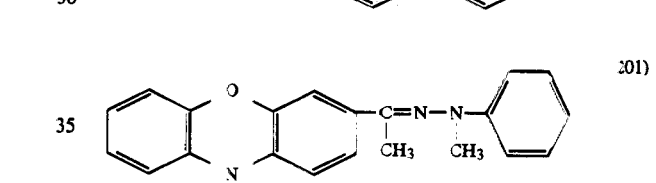 (202)
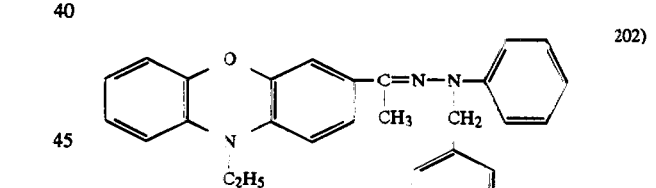 (203)
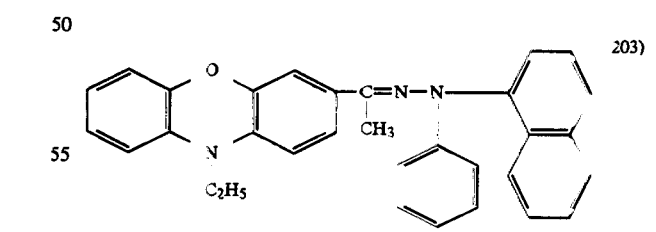 (204)

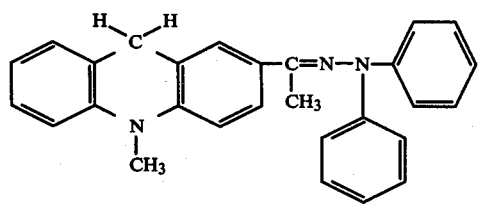 (205)
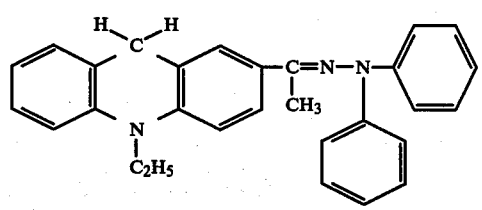 (206)
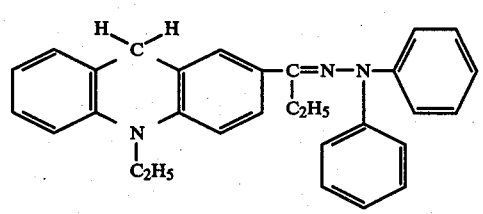 (207)
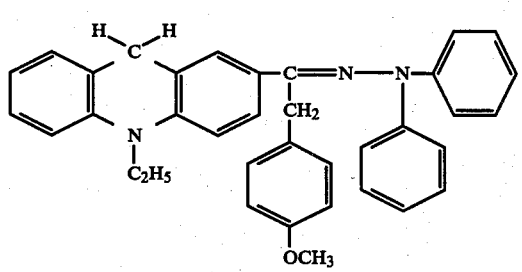 (208)
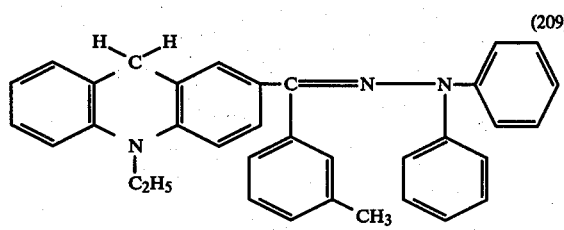 (209)
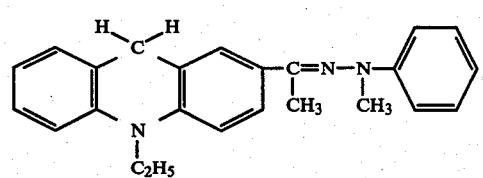 (210)
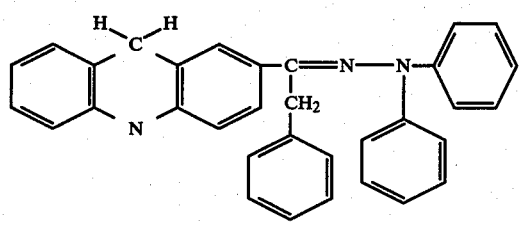 (211)
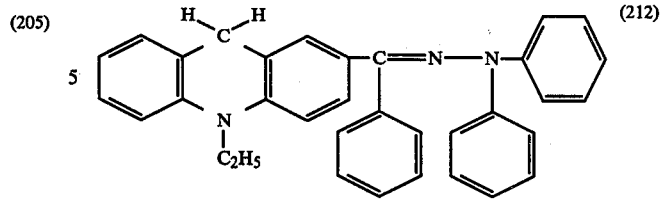 (212)
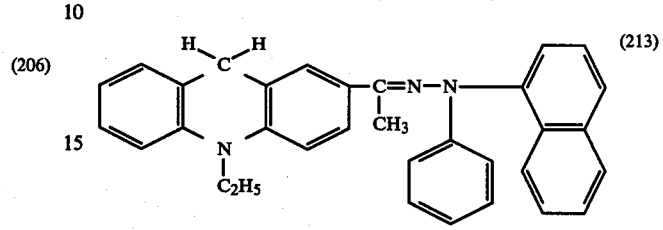 (213)
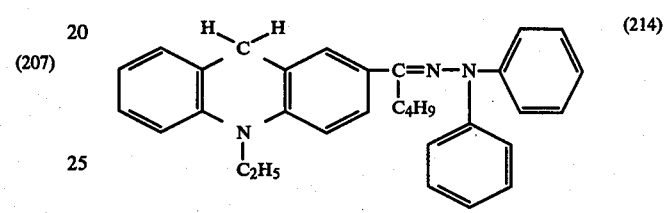 (214)
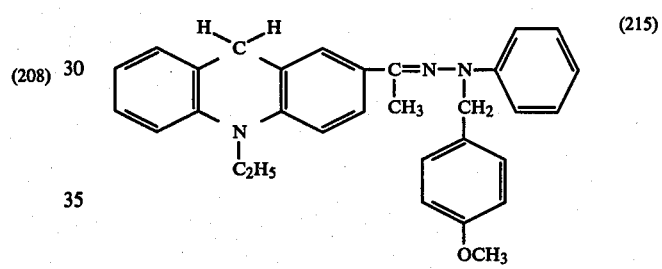 (215)
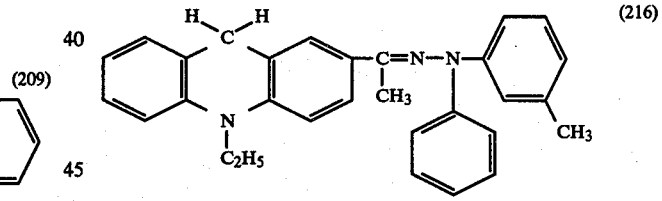 (216)
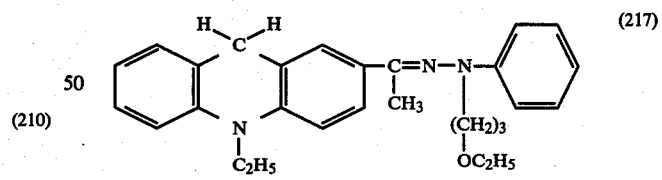 (217)
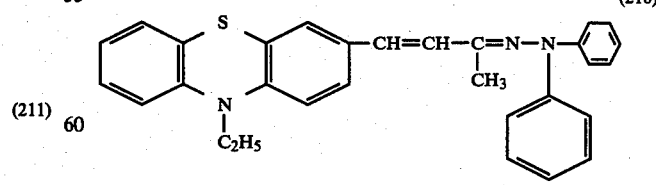 (218)
Hydrazone compounds represented by Formula (5)

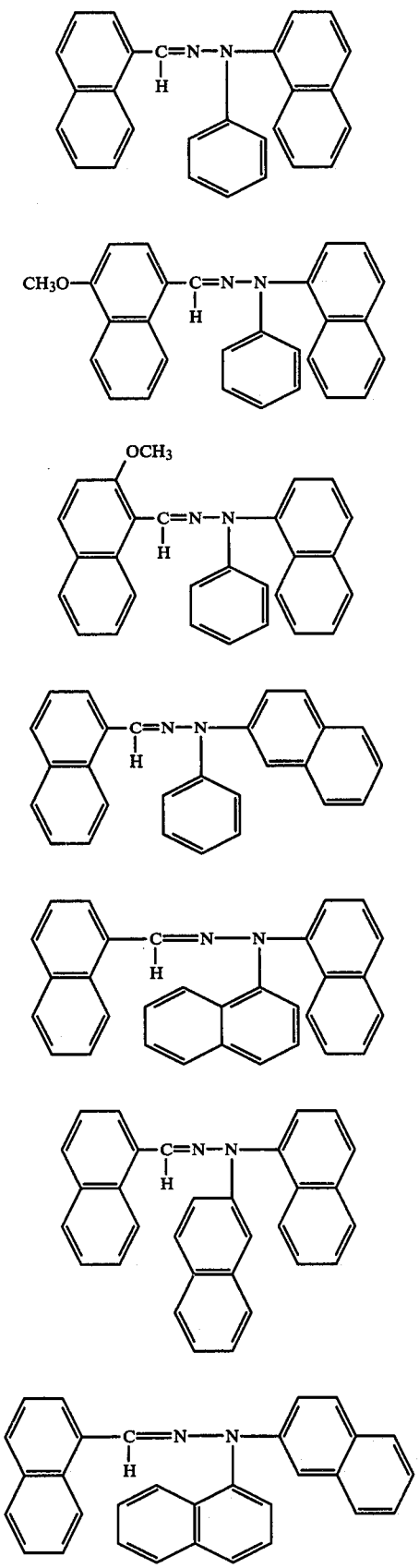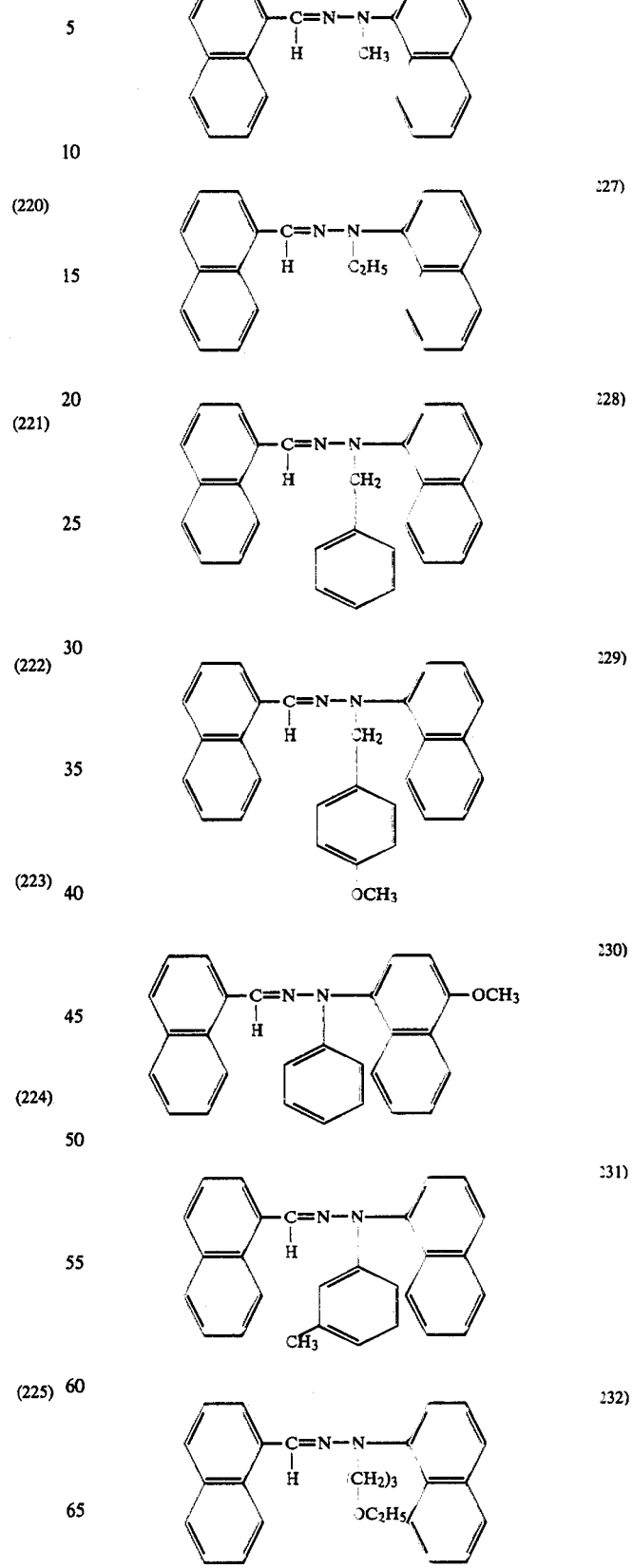

(233) (234) (235) (236) (237) (238) (239) (240) (241) (242)

(243)
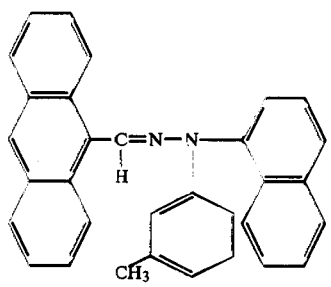
(244)
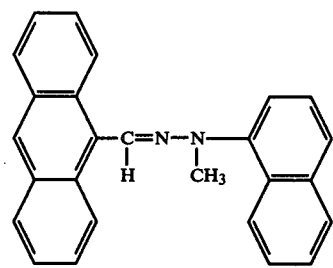
(245)
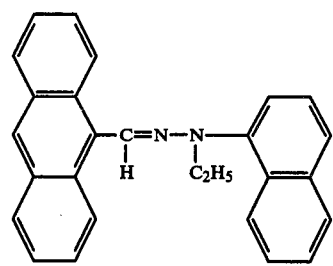
(246)
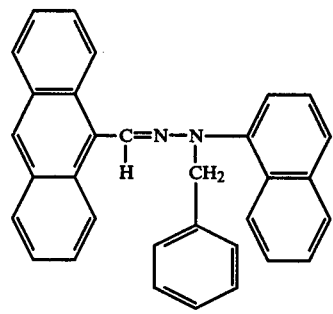
(247)
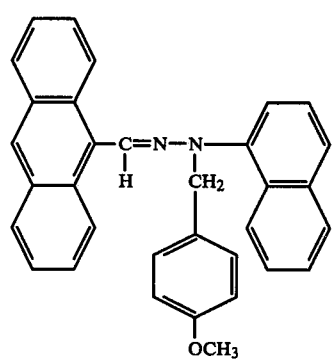
(243)
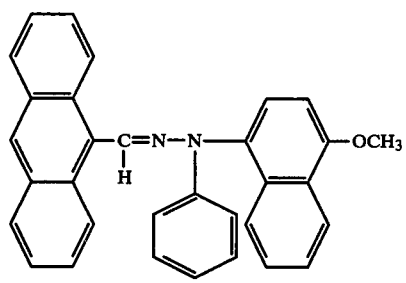
(248)
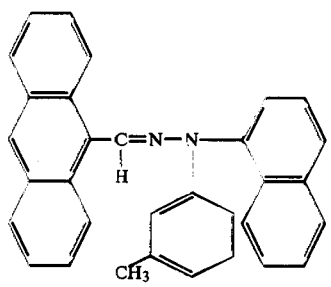
(249)
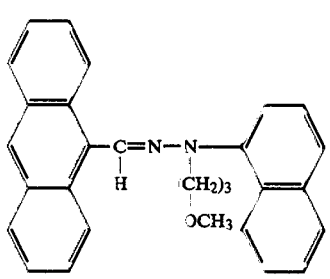
(250)
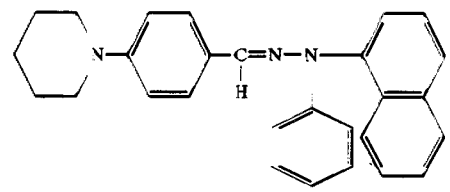
(251)
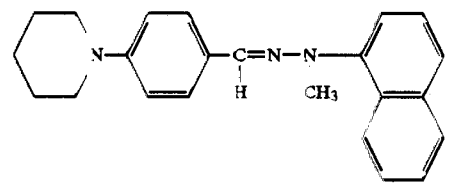
(252)
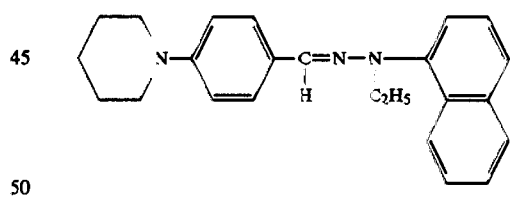
(253)
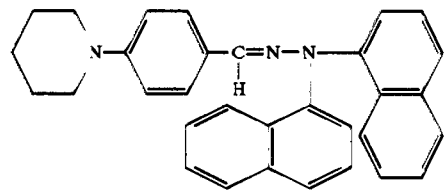
(254)
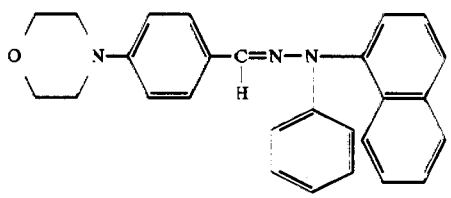

-continued

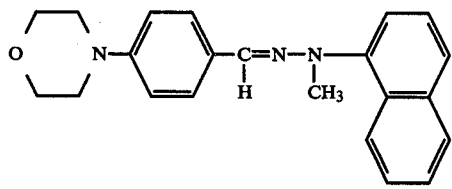 (255)

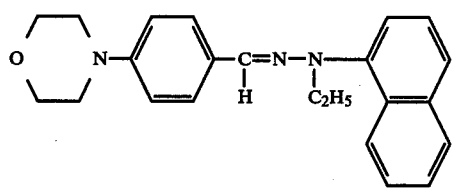 (256)

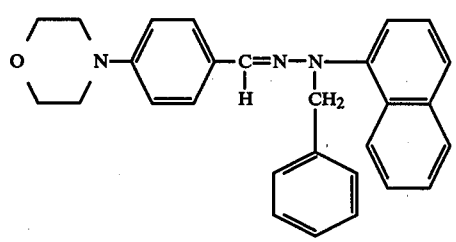 (257)

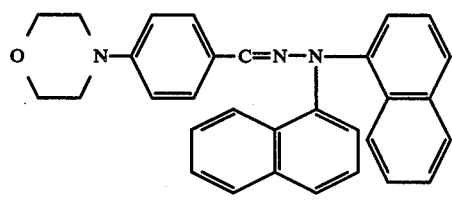 (258)

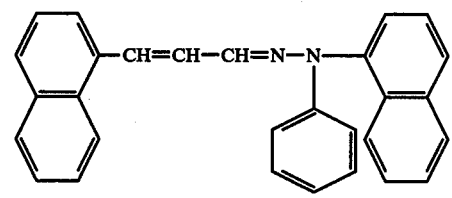 (259)

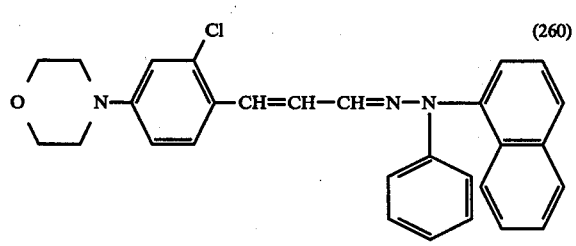 (260)

These hydrazone compounds can be used singly or in combination of two or more.

Hydrazone compounds represented by Formula (1) can be readily prepared by condensation of hydrazine compounds represented by the formula $$H_2N-N\begin{matrix}R_{13}\\R_{14}\end{matrix}$$

(wherein $R_{13}$ and $R_{14}$ are as defined above), with ketones represented by the formula

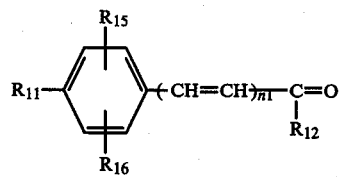

(wherein $R_{11}$, $R_{12}$, $R_{15}$, $R_{16}$, and $n_1$ are as defined above).

Preparation Examples are given below referring to typical hydrazone compounds used in this invention of Formula (1).

PREPARATION EXAMPLE 1 (Preparation of hydrazone compound No. 2 cited above)

In a 200-ml, three-necked flask were placed 2.8 g (0.012 mole) of N-phenyl-N-α-naphthylhydrazine, 2.3 g (0.012 mole) of a ketone represented by the formula

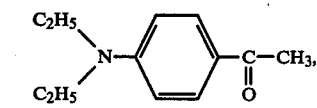

40 ml of ethanol, and 40 ml of acetic acid. The mixture was reacted at room temperature for 1 hour. Water was then added to the reaction mixture to form a precipitate, which was filtered and washed repeatedly with water. Recrystallization thereof from a methyl ethyl ketone-ethanol mixture gave 1.03 g of the intended hydrazone in yellow crystals, yield 21%.

Anal.(%). Calcd. for $C_{28}H_{29}N_3$: C 82.56, H 7.13, N 10.31; Found: C 82.51, H 7.14, N 10.35.

PREPARATION EXAMPLE 2 (Preparation of hydrazone compound No. 33 cited above)

In the same manner as in Preparation Example 1, 1.11 g (yield 23%) of the intended hydrazone in yellow crystals was obtained from 2.8 g (0.012 mole) of N-phenyl-N-p-methoxybenzylhydrazine and 2.3 g (0.012 mole) of a ketone represented by the formula (the same ketone as used in Preparation Example 1)

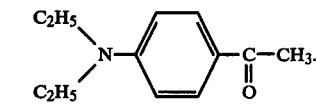

Anal.(%) Calcd. for $C_{26}H_{31}N_3O$: C 77.81, H 7.73, N 10.47; Found: C 77.83, H 7.75, N 10.46.

PREPARATION EXAMPLE 3 (PREPARATION OF HYDRAZONE COMPOUND NO. 59 CITED ABOVE)

In the same manner as in Preparation Example 1, 1.25 g (yield 24%) of the intended hydrazone in yellow crystals was obtained from 2.4 g (0.012 mole) of N-phenyl-N-benzylhydrazine and 3.0 g (0.012 mole) of a ketone represented by the formula

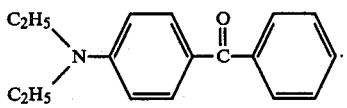

Anal.(%) Calcd. for $C_{30}H_{31}N_3$: C 83.14, H 7.16, N 9.70; Found: C 83.10, H 7.15, N 9.75.

PREPARATION EXAMPLE 4 (Preparation of hydrazone compound No. 85 cited above)

In the same manner as in Preparation Example 1, 1.14 g (yield 22%) of the intended hydrazone in yellow crystals was obtained from 2.2 g (0.012 mole) of N,N-diphenylhydrazine and 3.2 g (0.012 mole) of a ketone represented by the formula

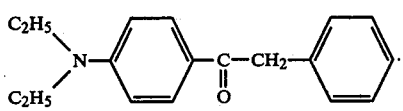

Anal.(%) Calcd. for $C_{30}H_{31}N_3$: C 83.14, H 7.16, N 9.70; Found: C 83.17, H 7.18, N 9.65.

Hydrazone compounds of Formula (2) can be readily prepared by condensation of hydrazine compounds represented by the formula

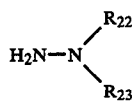

(wherein $R_{22}$ and $R_{23}$ are as defined above) with ketones represented by the formula

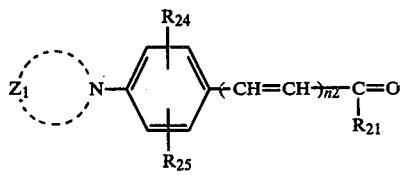

(wherein $Z_1$, $R_{21}$, $R_{24}$, $R_{25}$, and $n_2$ are as defined above).

An example is given below of the preparation of a typical hydrazone compound represented by Formula (2).

PREPARATION EXAMPLE 5 (Preparation of hydrazone compound No. 111 cited above)

In a 200-ml, three-necked flask were placed 2.2 g (0.012 mole) of N,N-diphenylhydrazine, 2.3 g (0.012 mole) of a ketone represented by the formula

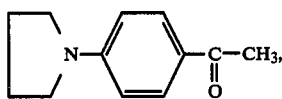

40 ml of ethanol, and 40 ml of acetic acid. The mixture was reacted at room temperature for 1 hour. The same after-treatments as applied in Preparation Example 1 gave 1.11 g of the intended hydrazone in yellow crystals, yield 26%.

Anal.(%) Calcd. for $C_{24}H_{25}N_3$: C 81.13, H 7.04, N 11.83; Found: C 81.10, H 7.02, N 11.88.

Hydrazone compounds of Formula (3) can be readily prepared by condensation of hydrazine compounds represented by the formula

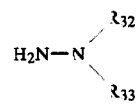

(wherein $R_{32}$ and $R_{33}$ are as defined above), with ketones represented by the formula

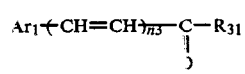

(wherein $Ar_1$, $R_{31}$, and $n_3$ are as defined above).

An example is given below of the preparation of a typical hydrazone compound represented by Formula (3).

PREPARATION EXAMPLE 6 (Preparation of hydrazone compound No. 150 cited above)

In a 200-ml, three-necked flask were placed 2.2 g (0.012 mole) of N,N-diphenylhydrazine, 2.0 g (0.012 mole) of a ketone represented by the formula

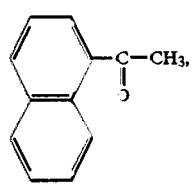

40 ml of ethanol, and 40 ml of acetic acid. The mixture was reacted at room temperature for 1 hour. The same after-treatments as applied in Preparation Example 1 gave 1.17 g of the intended hydrazone in yellow crystals, yield 29%.

Anal.(%) Calcd. for $C_{24}H_{20}N_2$: C 85.71, H 5.95, N 8.34; Found: C 85.76, H 5.93, N 8.31.

Hydrazone compounds of Formula (4) can be readily prepared by condensation of hydrazine compounds represented by the formula

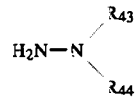

(wherein $R_{43}$ and $R_{44}$ are as defined above), with ketones represented by the formula

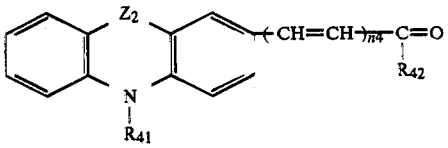

(wherein $Z_2$, $R_{41}$, $R_{42}$, and $n_4$ are as defined above).

An example is given below of the preparation of a typical hydrazone compound represented by the formula (4).

PREPARATION EXAMPLE 7 (Preparation of hydrazone compound No. 182 cited above)

In a 200-ml, three-necked flask were charged 2.2 g (0.012 mole) of N, N-diphenylhydrazine, 3.1 g (0.012 mole) of a ketone represented by the formula

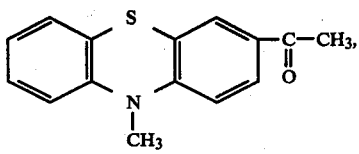

40 ml of ethanol, and 40 ml of acetic acid. The mixture was reacted at room temperature for 1 hour. The same after-treatments as applied in Preparation Example 1 gave 1.26 g of the intended hydrazone in yellow crystals, yield 25%.

Anal.(%) Calcd. for $C_{27}H_{23}N_3S$: C 76.96, H 5.46, N 9.98; Found: C 76.99, H 5.48, N 9.95.

Hydrazone compounds of Formula (5) can be readily prepared by condensation of hydrazine compounds represented by the formula

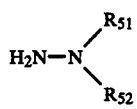

(wherein $R_{51}$ and $R_{52}$ are as defined above), with aldehydes represented by the formula

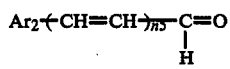

(wherein $Ar_2$ and $n_5$ are as defined above).

An example is given below of the preparation of a typical hydrazone compound represented by Formula (5).

PREPARATION EXAMPLE 8 (Preparation of hydrazone compound No. 219 cited above)

In a 200-ml, three-necked flask were charged 2.8 g (0.012 mole) of N-phenyl-N-α-naphthylhydrazine, 1.9 g (0.012 mole) of an aldehyde represented by the formula

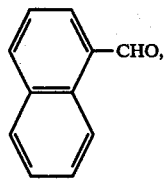

40 ml of ethanol, and 40 ml of acetic acid. The mixture was reacted at room temperature for 1 hour. The same after-treatments as applied in Preparation Example 1 gave 1.07 g of the intended hydrazone in yellow crystals, yield 24%.

Anal.(%) Calcd. for $C_{27}H_{20}N_2$: C 87.10, H 5.38, N 7.52; Found: C 87.14, H5.36, N 7.50.

Other hydrazone compounds used in this invention can be prepared in the same manner as illustrated above.

Hydrazone compounds of Formulas (1)–(5), though applicable to any electrophotographic photosensitive member using organic photoconductive material, are preferably used for the following types:

(1) The type comprising a charge-transfer complex of combination electron-donative and electron-attractive materials.

(2) The type comprising an organic photoconductive material sensitized with a dye.

(3) The type comprising a pigment dispersed in a hole matrix.

(4) The type comprising two separately functioning photosensitive layers: a charge generation layer and a charge transport layer.

(5) The type comprising the main components, an organic photoconductive material and a cocrystalline complex consisting of a dye and a resin.

(6) The type comprising a charge-transfer complex containing an organic or inorganic charge-generating material.

Of these types, (3)–(6) are preferable. In particular, when said hydrazone compound is used in photosensitive members of type (4), that is, comprising two separately functioning layers of charge generation and charge transport, the photosensitive members are improved in sensitivity and exhibit low residual potential. In addition, it becomes possible in this case to suppress the deterioration of sensitivity and the rise of residual potential for repeated operations to a practically negligible degree. Accordingly, the photosensitive member of type (4) will be described below in more detail.

It is essential for this type of photosensitive member to have a layer construction of conductive layer, charge generation layer, and charge transport layer. While the charge generation layer may be laid on either of the upper and lower sides of the charge transport layer, photosensitive members for repeated operations are preferred to have a layer construction laminated in order of conductive layer, charge generation layer, and charge transport layer from bottom to top, for mechanical strength and chargeability. A bond layer can be laid between the conductive layer and the charge generation layer as required for the purpose of improving adhesion between them.

Preferably, the charge transport layer in this invention is formed by coating a solution of both said hydrazone and a binder in a suitable solvent and drying it. Binders for use herein include polysulfone, acrylic resins, methacrylic resins, vinyl chloride resin, vinyl acetate resin, phenolic resins, epoxy resins, polyester resins, alkyd resins, polycarbonates, polyurethanes, and copolymers containing two or more kinds of repeating units of these resins, of which polyester resins and polycarbonates are particularly preferred. It is also possible to use, as the binder, photoconductive polymers such as poly(N-vinylcarbazole) which themselves have charge-transporting ability.

The compounding ratio of the charge-transporting compound to the binder is desirably in the range of 10:100 to 500:100 by weight. Thickness of the charge tranport layer is generally 2–100μ, preferably 5–30μ. The charge transport layer can be formed by usual coating methods including blade coating, Meyer bar coating, spray coating, dip coating, bead coating, air-knife coating, and the like.

Various organic solvents can be used for the coating to form the charge transport layer of this invention. Typical solvents thereof are aromatic hydrocarbons e.g., benzene, toluene, xylene, mesitylene, chlorobenzene, and the like; ketones e.g., acetone, 2-butanone, and the like; halogenated aliphatic hydrocarbons e.g., methylene chloride, chloroform, ethylene chloride, and the like; cyclic or linear ethers e.g., tetrahydrofuran, ethyl ether, and the like; and mixtures of these solvents.

The charge transport layer of this invention can contain various additives, for example, diphenyl, o-terphenyl, p-terphenyl, dibutyl phthalate, dimethylglycol phthalate, dioctyl phthalate, triphenyl phosphate, methylnaphthalene, benzophenone, chlorinated paraffin, dilauryl thiodipropionate, 3,5-dinitrosalicyclic acid, various kinds of fluorocarbons, silicone oils, silicone rubbers, and phenolic compounds such as 3,5-di-t-butyl-4-hydroxytoluene, 2,2'-methylene bis(6-t-butyl-4-methylphenol), α-tocopherol, 2-t-octyl-5-chlorohydroquinone, 2,5-di-t- octylhydroquinone, and the like.

For the charge generation layer, any charge-generating material can be used that absorbs light to generate charge carriers at a very high efficiency. Such materials preferred include inorganic substances such as selenium, selenium-tellurium, selenium-arsenic, cadmium sulfide, amorphous silicon, and the like and organic substances such as pyrylium dyes, thiopyrylium dyes, triarylmethane dyes, thiazine dyes, cyanine dyes, phthalocyanine pigments, perylene pigments, indigo pigments, thioindigo pigments, quinacridone pigments, squaric acid pigments, azo pigments, polycyclic quinone pigments, and the like.

Typical examples of charge-generating materials usable in this invention are given below.

(1) Amorphous silicon
(2) Selenium - tellurium
(3) Selenium - arsenic
(4) Cadmium sulfide (5) 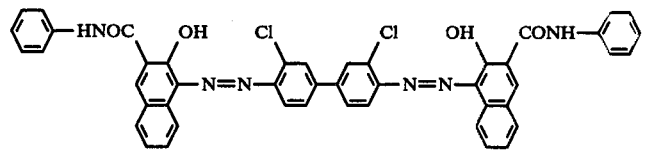

(6) 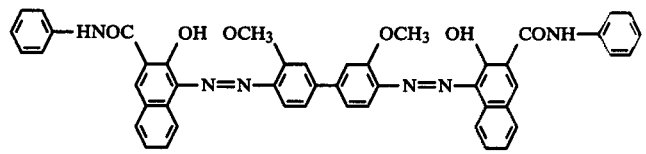

(7) 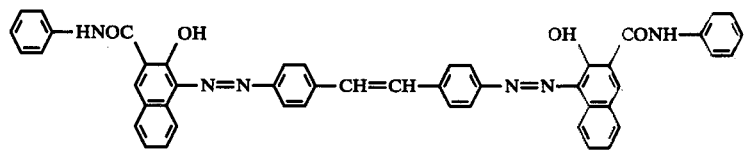

(8) 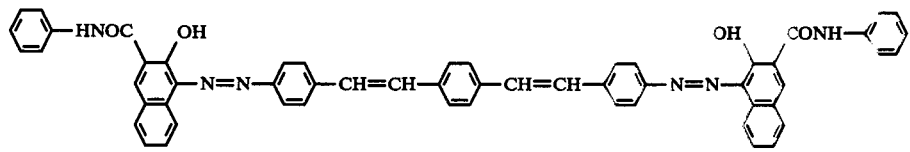

(9) 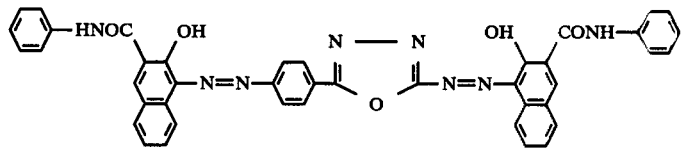

(10) 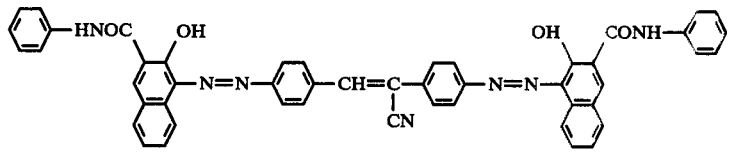

-continued
(11) 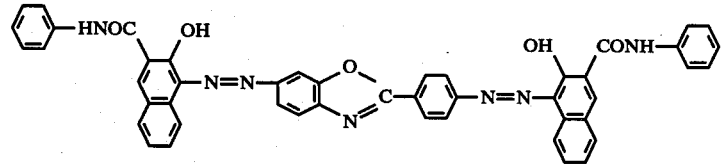
(12) 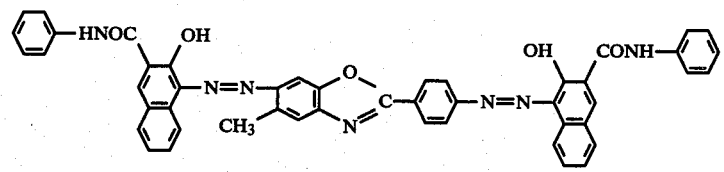
(13) 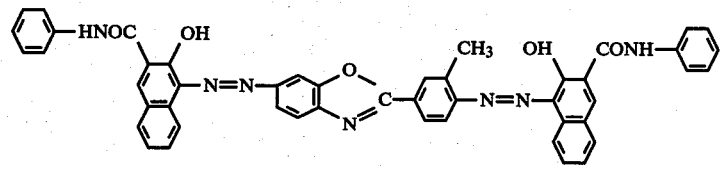
(14) 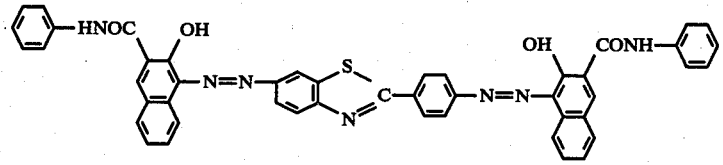
(15) 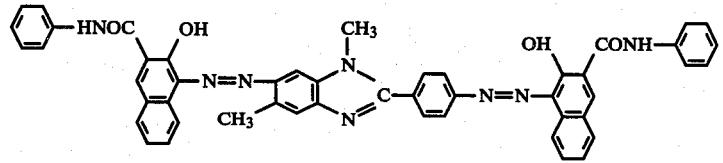
(16) 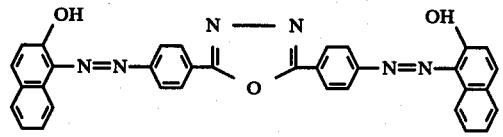
(17) 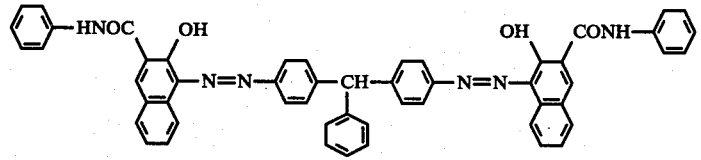
(18) 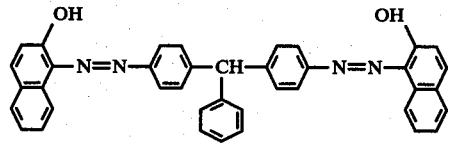
(19) 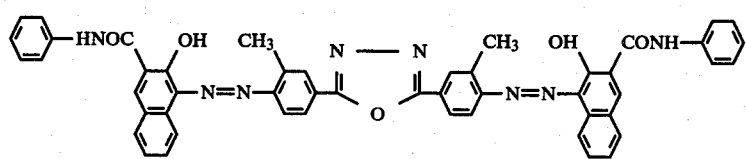

-continued
(20) 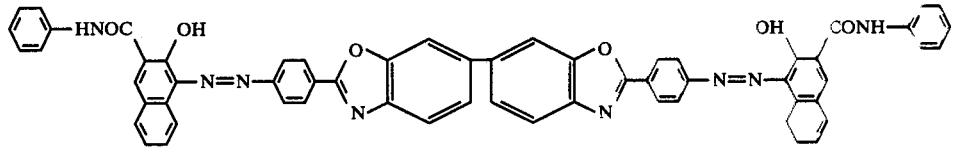
(21) 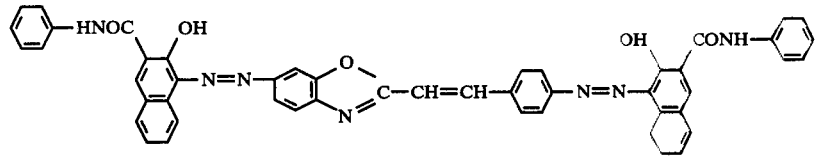
(22) 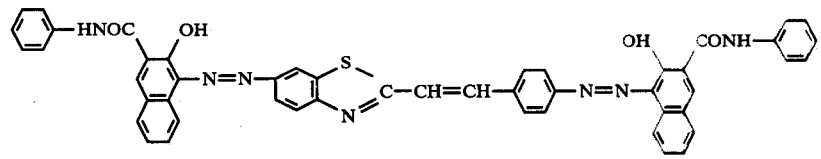
(23) 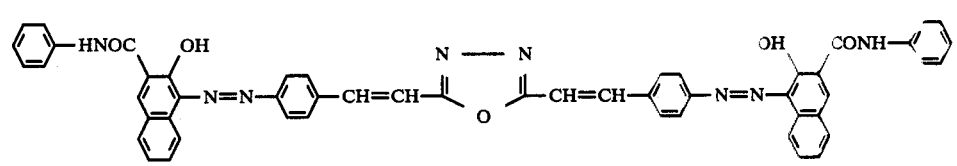
(24) 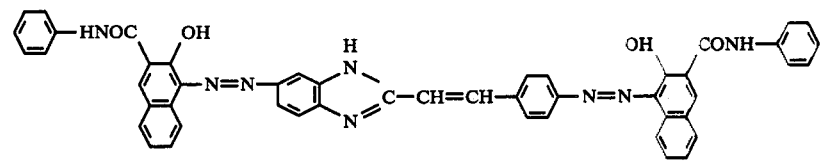
(25) 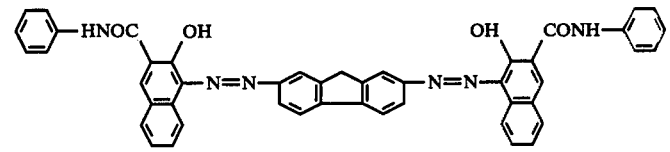
(26) 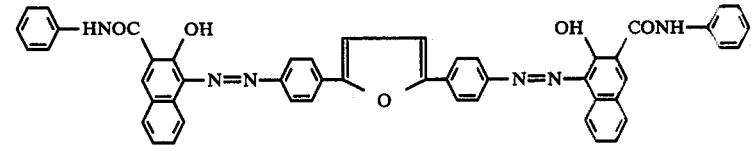
(27) 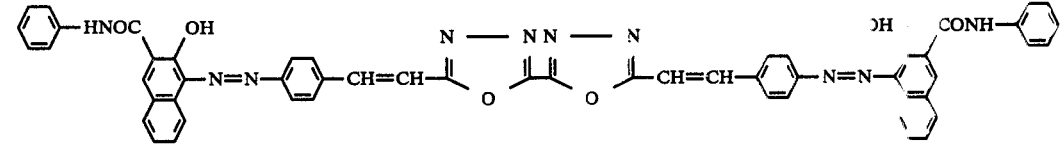
(28) 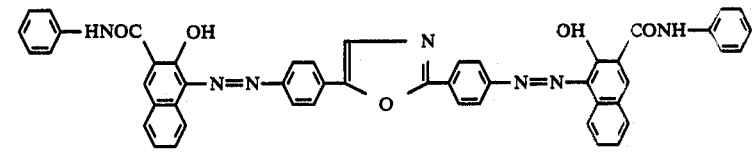

-continued
(29) 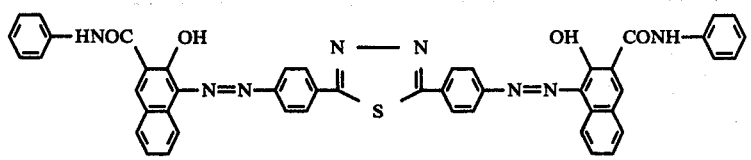
(30) 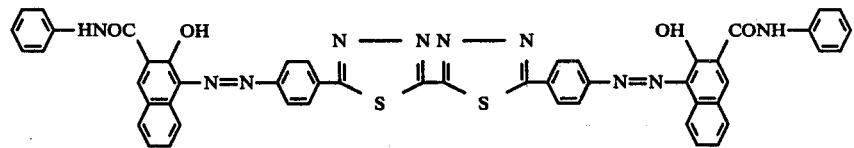
(31) 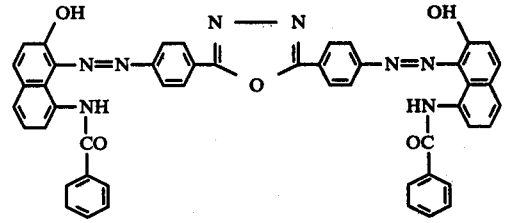
(32) 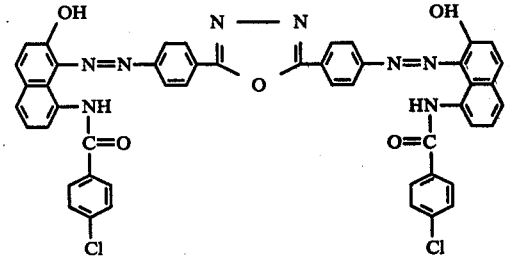
(33) 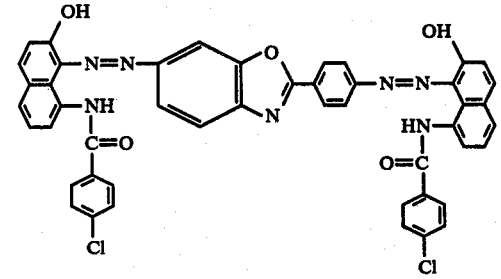
(34) 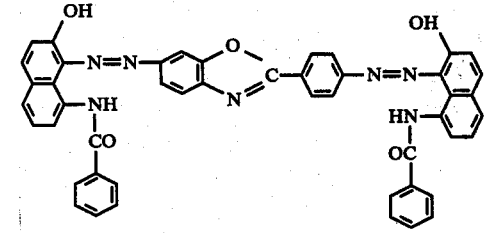
(35) 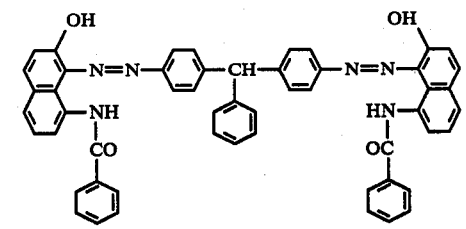

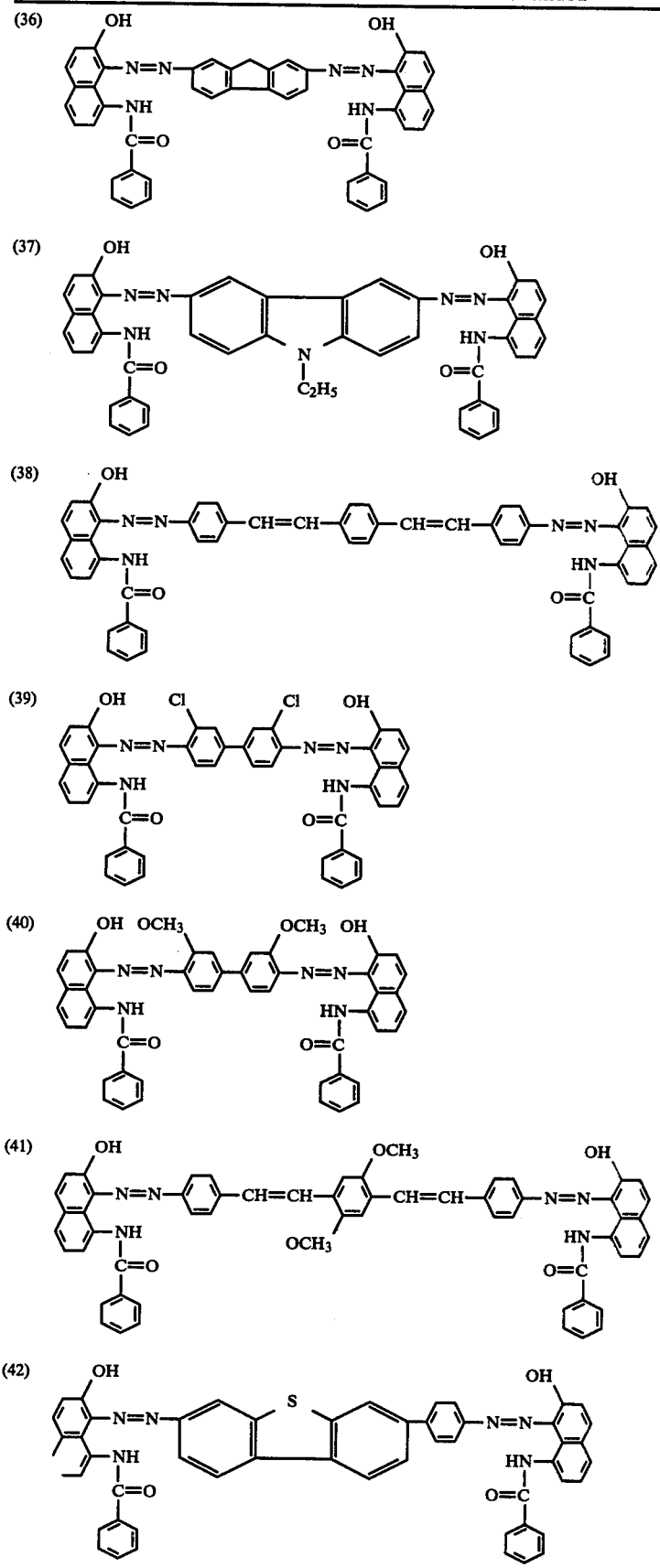

-continued
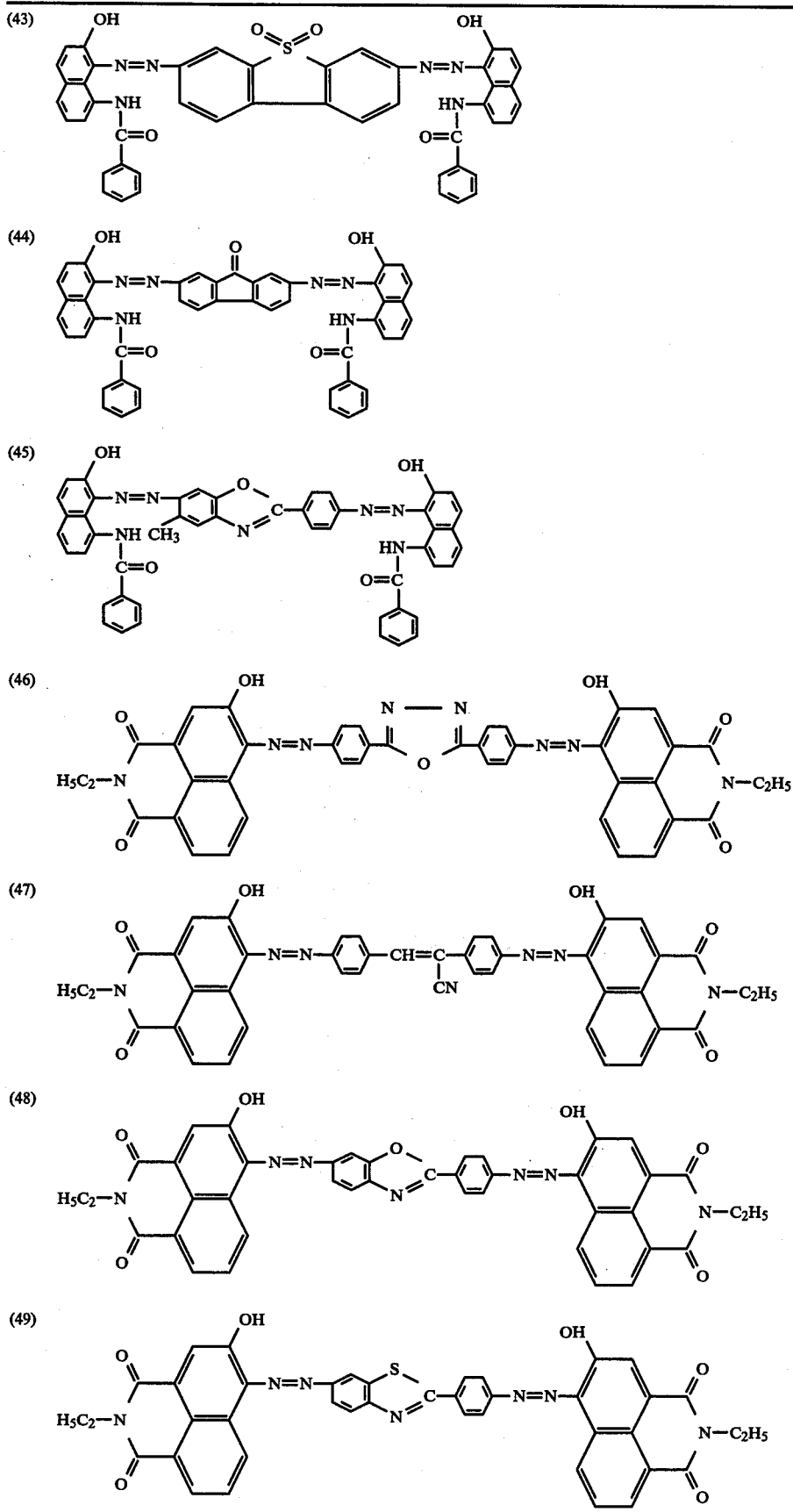

(50) 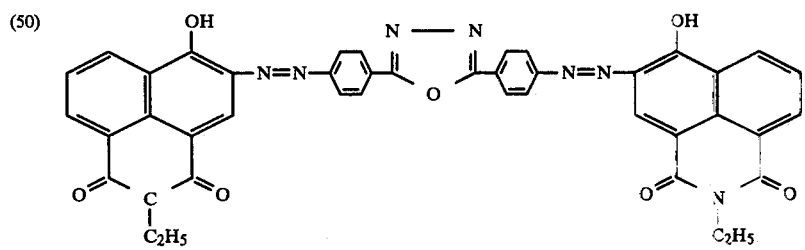
(51) 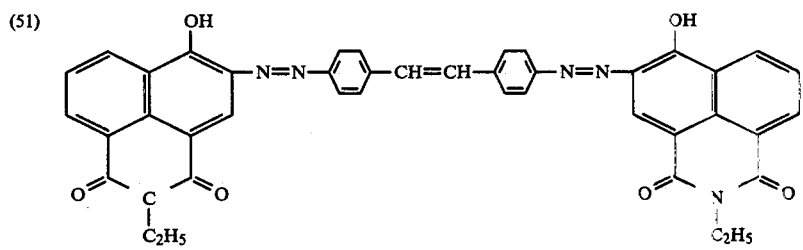
(52) 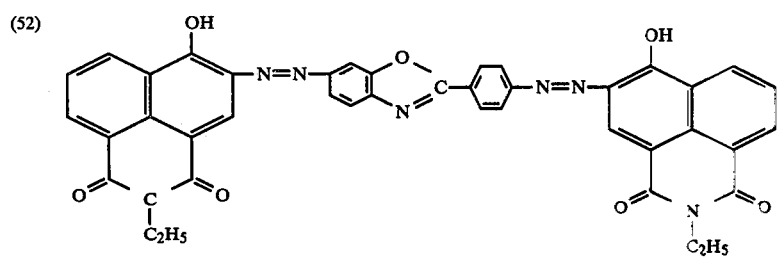
(53) 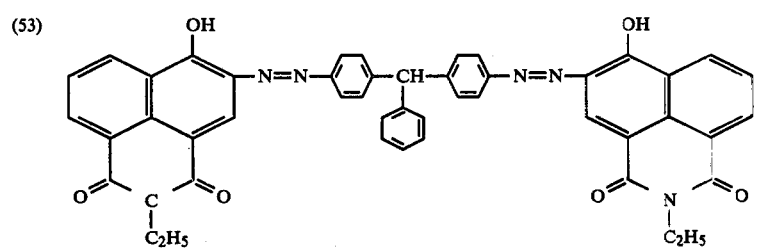
(54) 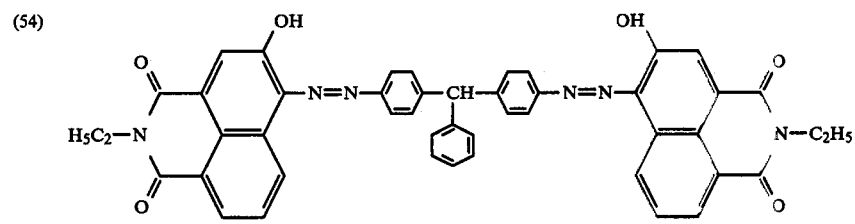
(55) 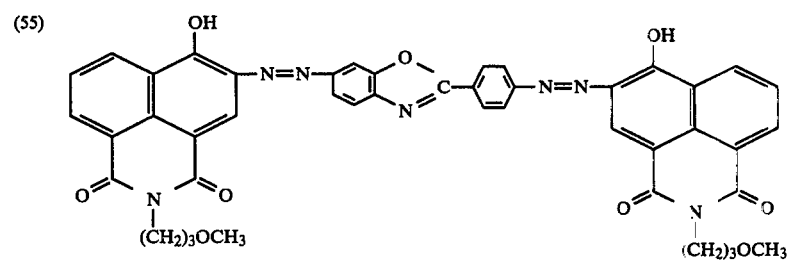

(56) 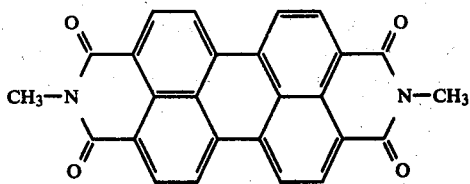

(57) 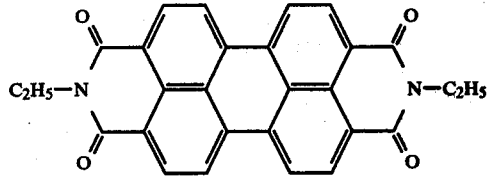

(58) Methine dyes derived from squaric acid
(59) Indigo dye (C.I. No. 78000)
(60) Thioindigo dye (C.I. No. 78800)
(61) B-Type copper phthalocyanine
(62) ε-Type copper phthalocyanine

(63) 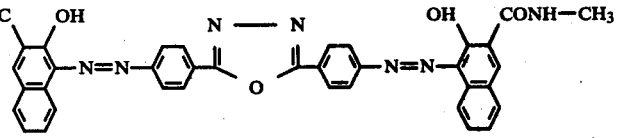

(64) 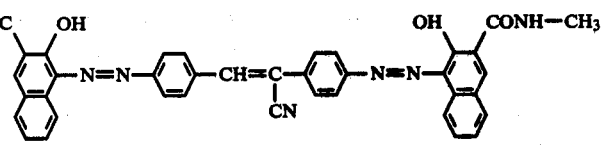

(65) 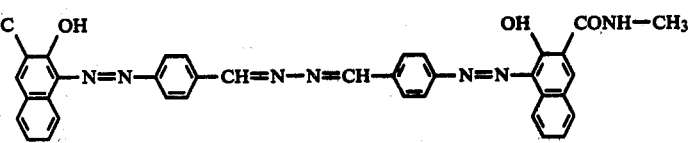

(66) 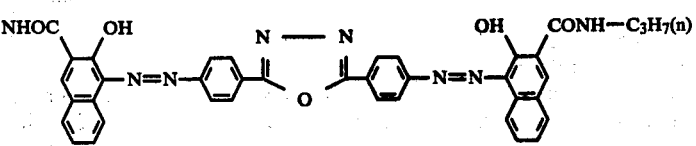

These pigments or dyes can be used singly or in combination of two or more.

The electrophotographic photosensitive member of this invention can be prepared by covering a suitable conductive substrate with a charge generation layer containing said pigment and then coating this layer with a charge transport layer as described above. This type of electrophotographic photosensitive member may also be provided with an intermediate layer between the conductive substrate and the charge generation layer. This intermediate layer bars the injection of free charge from the conductive substrate into the photosensitive layer having layer construction, when the photosensitive layer is charged, and also acts as a bond layer to fasten the photosensitive layer to the conductive substrate. The intermediate layer can be formed of a metal oxide such as aluminum oxide, polyethylene, polypropylene, acrylic resins, methacrylic resins, vinyl chloride resin, phenolic resins, epoxy resins, polyester resins, alkyd resins, polycarbonates, polyurethanes, polyimide resins, vinylidene chloride resin, vinyl chloride-vinyl acetate copolymer, casein, gelatin, poly(vinyl alcohol), nitrocellulose, water-soluble ethylene-acrylic acid copolymer, or the like. Thickness of the intermediate layer is in the range of 0.1 to 5μ, preferably 0.5 to 3μ. The charge generation layer can also be laid on the upper side of the charge transport layer. In this case a suitable surface protecting layer may be provided for surface protection.

The charge generation can be formed by a suitable method selected, depending on the type of charge-generating material to be used, from the vacuum deposition method, the sputtering method, the glow discharge, usual coating methods, and the like.

The coating can be effected by applying a binder-free charge-generating material, a dispersion of a charge generating material in a resin solution, or a homogeneous solution of both a charge-generating material and a binder.

Known means such as ball mills, attritors, and the like can be used for dispersing the charge-generating pigment or dye, wherein its particle sizes are reduced to 5μ or less, more preferably 2μ or less, and most preferably 0.5μ or less.

The pigment can also be applied in the form of solution in an amine solvent such as ethylenediamine and the like. The coating can be carried out by usual methods including blade coating, Meyer bar coating, spray coating, dip coating, etc.

Thickness of the charge generating layer in this invention ranges 5μ or less, preferably 0.01–1μ.

Binders for use in the dispersion of the above-mentioned charge-generating materials include poly(vinyl butyral), poly(methyl methacrylate), polyesters, poly(-vinylidene chloride), polyamides, chlorinated rubber, polyvinyltoluene, polystyrene, poly(vinyl chloride), ethyl cellulose, polyvinylpyridine, styrene-maleic anhydride copolymer, and the like. The binder content in the charge generation layer is up to 80%, preferably 50% or less, by total weight of the layer.

The surface of the charge generation layer may be subjected to mirror finishing, if necessary, for the purpose of making uniform the injection of carrier from the charge generation layer into the upper charge transport layer.

For operating the photosensitive member of this invention comprising a conductive layer, charge generation layer, and charge transport layer laminated in this order, the surface of the charge transport layer needs to be negatively charged since the hydrazone compound used in the present invention is of a hole-transporting property. On image exposure of the photosensitive member after negative charging, holes generated in the exposed area of the charge generation layer are injected into the charge transport layer, then arrive the surface thereof, and neutralize the negative charge thereof to decay the surface potential, thus producing an electrostatic contrast between the exposed and unexposed areas.

Various conventional developing processes can be employed for visualizing the latent image.

Another preferred embodiment (the foregoing type 3) of this invention employing the above-mentioned hydrazone compound is an electrophotographic photosensitive member comprising a conductive layer overlaid with a photosensitive layer formed from a dispersion of the foregoing pigment in a charge-transporting medium consisting mainly of the above-mentioned hydrazone compound as a charge transporting material and an insulating binder [the binder itself may be a charge-transporting substance, like poly(N-vinylcarbazole)]. The binder and charge-generating material disclosed in U.S. Pat. Nos. 3,894,868 and 3,870,516 can be used in this case.

The substrate usable in the electrophotographic photosensitive member of this invention may be constructed with any material having an adequate conductivity; that is, there may be used any type of conventional conductive substrate, including sheets of metals such as aluminum, vanadium, molybdenum, chromium, cadmium, titanium, nickel, copper, zinc, palladium, indium, tin, platinum, gold, stainless steel, brass, and the like, plastic sheets on which these metals are vacuum-deposited or laminated, and the like.

The electrophotographic photosensitive member of this invention can be utilized not only in electrophotographic copying machines but also over a wide field of electrophotographic apparatus such as laser printers, CRT printers, electrophotographic printing plate making systems, etc.

The electrophotographic photosensitive member of this invention has advantages over those employing conventional organic photoconductive materials, in that it exhibits a higher initial potential, less dark decay, and impoved photomemory property, thus being more effective in practical applications.

This invention will be illustrated in more detail referring to the following Examples:

EXAMPLE 1

A solution of casein in aqueous ammonia (casein 11.2 g, 28% aqueous ammonia 1 g, water 222 ml) was coated on an aluminum plate by means of a Meyer bar and dried to form a bond layer of 1.0 g/m² in coating weight.

A disazo pigment (5 g) having the structure

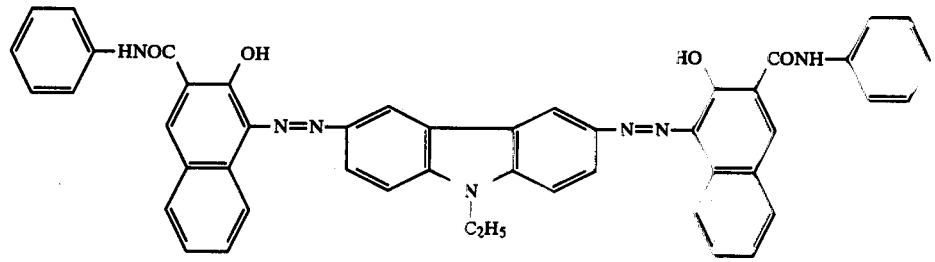

was dispersed in a solution of 2 g of a vinyl butyral resin (degree of butyral conversion 63 mole %) in 95 ml of ethanol. The dispersion was coated on the bond layer and dried to form a charge generation layer of 0.2 g/m² in coating weight.

A solution of hydrazone compound No. 2 (5 g) cited above and 5 g of a polycarbonate [poly(carbonic acid ester of bisphenol A)] (viscosity average mol.wt. about 30,000) in 150 ml of dichloromethane, was coated on the charge generation layer and dried to form a charge transport layer of 10 g/m² in coating weight.

The electrophotographic photosensitive member thus prepared was measured for initial potential, sensitivity, dark decay, and photomemory property by using an electrostatic copying paper testing machine (Model SP-408, mfd. by Kawaguchi Denki Co., Ltd.). The initial potential ($V_o$) was measured by corona-charging the specimen therewith at $-5$ KV in the static fashion. The dark decay was evaluated by measuring the potential ($V_5$) of the charged specimen after 5-second standing in the dark, the sensitivity by measuring the exposure light quantity ($E_{\frac{1}{2}}$, lux.sec) for halving $V_5$, and the photomemory property ($P_M$) by measuring the time required for specimen to recover its original charge bearing characteristics after exposured for 5 minutes at an illumination intensity of 1000 lux. Results thereof are shown in Table 1.

TABLE 1

| | |
|---|---|
| $V_0$ | −590 volt |
| $V_5$ | −570 volt |
| $P_M$ | 2 min. |
| $E_{\frac{1}{2}}$ | 4.6 lux · sec. |

EXAMPLES 2–135

Electrophotographic photosensitive members were prepared and measured for charge bearing characteristics, in the same manner as in Example 1 except for using the hydrazone compounds shown in Table 2 in place of the hydrazone compound No. 2. Results thereof are shown in Table 2.

TABLE 2

| Example No. | Hydrazone compound | $V_0$ (volt) | $V_5$ (volt) | $P_M$ (min.) | $E_{\frac{1}{2}}$ (lux · sec.) |
|---|---|---|---|---|---|
| 2 | No. (5) | −580 | −560 | 2 | 4.7 |
| 3 | No. (6) | −590 | −570 | 2 | 4.7 |
| 4 | No. (7) | −570 | −550 | 2 | 5.3 |
| 5 | No. (8) | −570 | −550 | 3 | 5.2 |
| 6 | No. (9) | −590 | −560 | 2 | 4.2 |
| 7 | No. (10) | −580 | −560 | 3 | 4.0 |
| 8 | No. (13) | −560 | −550 | 2 | 5.5 |
| 9 | No. (16) | −560 | −540 | 2 | 5.0 |
| 10 | No. (17) | −590 | −560 | 2 | 4.1 |
| 11 | No. (19) | −570 | −560 | 2 | 4.9 |
| 12 | No. (20) | −560 | −540 | 2 | 5.5 |
| 13 | No. (22) | −590 | −570 | 3 | 3.9 |
| 14 | No. (23) | −560 | −550 | 2 | 8.2 |
| 15 | No. (25) | −570 | −550 | 2 | 9.8 |
| 16 | No. (26) | −590 | −560 | 3 | 7.6 |
| 17 | No. (28) | −560 | −540 | 2 | 10.6 |
| 18 | No. (29) | −570 | −550 | 2 | 8.4 |
| 19 | No. (30) | −580 | −550 | 2 | 6.1 |
| 20 | No. (33) | −590 | −570 | 2 | 4.5 |
| 21 | No. (36) | −580 | −550 | 2 | 4.3 |
| 22 | No. (37) | −580 | −560 | 2 | 4.7 |
| 23 | No. (38) | −590 | −570 | 2 | 4.9 |
| 24 | No. (39) | −570 | −550 | 2 | 5.3 |
| 25 | No. (40) | −570 | −550 | 2 | 4.5 |
| 26 | No. (43) | −590 | −570 | 3 | 4.0 |
| 27 | No. (44) | −580 | −560 | 2 | 4.3 |
| 28 | No. (45) | −600 | −580 | 2 | 3.5 |
| 29 | No. (47) | −570 | −550 | 2 | 5.0 |
| 30 | No. (48) | −570 | −550 | 2 | 5.4 |
| 31 | No. (50) | −560 | −550 | 2 | 5.5 |
| 32 | No. (51) | −580 | −560 | 2 | 3.7 |
| 33 | No. (52) | −560 | −540 | 2 | 15.1 |
| 34 | No. (53) | −570 | −550 | 3 | 14.9 |
| 35 | No. (54) | −570 | −550 | 2 | 14.6 |
| 36 | No. (55) | −580 | −560 | 2 | 14.8 |
| 37 | No. (56) | −580 | −570 | 2 | 14.4 |
| 38 | No. (59) | −570 | −550 | 2 | 4.6 |
| 39 | No. (62) | −590 | −560 | 2 | 4.3 |
| 40 | No. (63) | −560 | −540 | 2 | 5.2 |
| 41 | No. (65) | −580 | −560 | 2 | 4.5 |
| 42 | No. (66) | −560 | −530 | 3 | 4.6 |
| 43 | No. (67) | −570 | −550 | 2 | 5.0 |
| 44 | No. (69) | −590 | −570 | 3 | 4.0 |
| 45 | No. (72) | −580 | −550 | 2 | 4.5 |
| 46 | No. (74) | −570 | −550 | 2 | 8.7 |
| 47 | No. (75) | −580 | −550 | 2 | 11.4 |
| 48 | No. (76) | −560 | −540 | 2 | 12.7 |
| 49 | No. (79) | −580 | −560 | 2 | 10.3 |
| 50 | No. (82) | −570 | −540 | 2 | 12.0 |
| 51 | No. (85) | −570 | −550 | 2 | 5.3 |
| 52 | No. (88) | −570 | −550 | 2 | 5.5 |
| 53 | No. (89) | −560 | −540 | 2 | 5.3 |
| 54 | No. (90) | −570 | −550 | 2 | 4.8 |
| 55 | No. (92) | −580 | −550 | 2 | 5.0 |
| 56 | No. (93) | −580 | −560 | 3 | 4.6 |
| 57 | No. (94) | −570 | −550 | 2 | 4.7 |
| 58 | No. (98) | −570 | −560 | 2 | 5.4 |
| 59 | No. (103) | −560 | −540 | 2 | 12.3 |
| 60 | No. (104) | −570 | −550 | 2 | 14.0 |
| 61 | No. (105) | −580 | −560 | 2 | 8.9 |
| 62 | No. (107) | −580 | −550 | 2 | 7.8 |
| 63 | No. (111) | −590 | −560 | 2 | 4.6 |
| 64 | No. (115) | −600 | −570 | 2 | 4.3 |
| 65 | No. (117) | −580 | −560 | 2 | 4.9 |
| 66 | No. (120) | −590 | −570 | 2 | 4.7 |
| 67 | No. (125) | −600 | −580 | 2 | 4.2 |
| 68 | No. (127) | −590 | −570 | 2 | 4.0 |
| 69 | No. (128) | −560 | −540 | 3 | 5.5 |
| 70 | No. (130) | −580 | −560 | 2 | 4.1 |
| 71 | No. (131) | −560 | −540 | 3 | 5.8 |
| 72 | No. (132) | −570 | −550 | 2 | 4.9 |
| 73 | No. (133) | −580 | −550 | 2 | 4.5 |
| 74 | No. (134) | −570 | −550 | 2 | 4.6 |
| 75 | No. (136) | −580 | −560 | 2 | 4.3 |
| 76 | No. (137) | −580 | −560 | 2 | 4.1 |
| 77 | No. (140) | −600 | −570 | 2 | 3.9 |
| 78 | No. (142) | −600 | −580 | 2 | 3.7 |
| 79 | No. (143) | −580 | −560 | 2 | 4.5 |
| 80 | No. (147) | −590 | −570 | 2 | 4.0 |
| 81 | No. (150) | −590 | −570 | 2 | 4.8 |
| 82 | No. (154) | −580 | −550 | 2 | 4.6 |
| 83 | No. (157) | −590 | −560 | 2 | 5.0 |
| 84 | No. (158) | −590 | −560 | 2 | 4.7 |
| 85 | No. (160) | −560 | −540 | 2 | 4.8 |
| 86 | No. (162) | −570 | −550 | 2 | 5.2 |
| 87 | No. (166) | −580 | −560 | 2 | 5.1 |
| 88 | No. (168) | −590 | −560 | 3 | 4.0 |
| 89 | No. (170) | −580 | −560 | 2 | 4.1 |
| 90 | No. (173) | −610 | −590 | 2 | 4.4 |
| 91 | No. (174) | −580 | −560 | 2 | 5.1 |
| 92 | No. (175) | −590 | −570 | 2 | 4.5 |
| 93 | No. (178) | −570 | −550 | 3 | 3.7 |
| 94 | No. (179) | −580 | −550 | 2 | 4.2 |
| 95 | No. (182) | −570 | −550 | 2 | 5.6 |
| 96 | No. (184) | −580 | −560 | 2 | 5.2 |
| 97 | No. (185) | −570 | −550 | 2 | 5.8 |
| 98 | No. (186) | −560 | −550 | 2 | 6.2 |
| 99 | No. (188) | −570 | −550 | 2 | 5.4 |
| 100 | No. (189) | −570 | −540 | 2 | 5.5 |
| 101 | No. (190) | −580 | −560 | 2 | 5.0 |
| 102 | No. (191) | −570 | −550 | 2 | 4.8 |
| 103 | No. (192) | −580 | −560 | 3 | 4.5 |
| 104 | No. (193) | −560 | −540 | 2 | 5.7 |
| 105 | No. (194) | −570 | −550 | 3 | 5.3 |
| 106 | No. (195) | −580 | −560 | 2 | 4.7 |
| 107 | No. (196) | −570 | −550 | 3 | 4.8 |
| 108 | No. (199) | −570 | −560 | 2 | 5.4 |
| 109 | No. (200) | −570 | −550 | 2 | 5.6 |
| 110 | No. (201) | −560 | −540 | 2 | 5.9 |
| 111 | No. (202) | −560 | −540 | 2 | 6.2 |
| 112 | No. (203) | −570 | −550 | 2 | 4.7 |
| 113 | No. (205) | −570 | −550 | 2 | 5.2 |
| 114 | No. (206) | −580 | −560 | 3 | 4.6 |
| 115 | No. (210) | −560 | −550 | 2 | 5.9 |
| 116 | No. (211) | −570 | −550 | 2 | 6.3 |
| 117 | No. (212) | −570 | −560 | 2 | 5.7 |
| 118 | No. (213) | −580 | −560 | 2 | 4.5 |
| 119 | No. (219) | −570 | −550 | 2 | 8.0 |
| 120 | No. (220) | −590 | −570 | 2 | 6.1 |
| 121 | No. (222) | −580 | −560 | 2 | 7.2 |
| 122 | No. (226) | −580 | −550 | 2 | 8.3 |
| 123 | No. (228) | −580 | −560 | 2 | 11.2 |
| 124 | No. (234) | −580 | −560 | 2 | 6.7 |
| 125 | No. (236) | −590 | −560 | 2 | 4.0 |
| 126 | No. (239) | −590 | −570 | 2 | 8.2 |
| 127 | No. (244) | −550 | −540 | 2 | 9.2 |
| 128 | No. (246) | −570 | −550 | 2 | 5.7 |
| 129 | No. (247) | −590 | −560 | 3 | 6.9 |
| 130 | No. (250) | −580 | −560 | 2 | 4.4 |
| 131 | No. (251) | −570 | −550 | 2 | 5.0 |
| 132 | No. (253) | −580 | −550 | 2 | 4.8 |
| 133 | No. (254) | −570 | −560 | 2 | 4.9 |
| 134 | No. (255) | −580 | −560 | 3 | 5.0 |
| 135 | No. (257) | −570 | −550 | 2 | 4.7 |
| 136 | No. (258) | −590 | −570 | 2 | 4.3 |

COMPARATIVE EXAMPLES 1-8

Electrophotographic photosensitive members for comparison were prepared and measured for charge bearing characteristics in the same manner as in Example 1 except using each of the following hydrazone compounds (A)-(H) in place of the hydrazone compound No. 2.

(A) 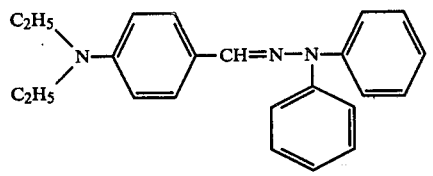

(B) 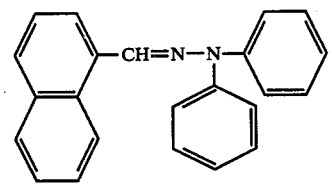

(C) 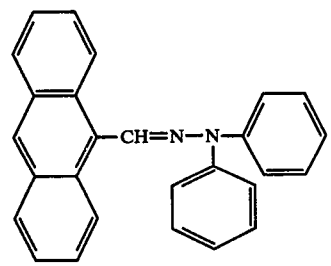

(D) 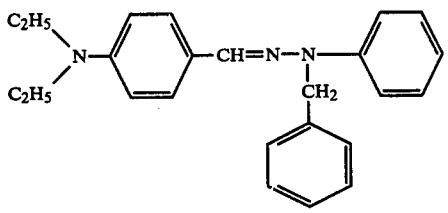

(E) 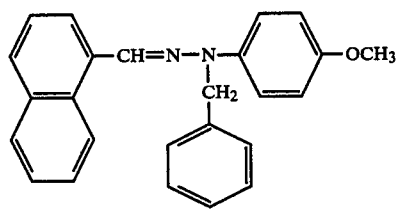

(F) 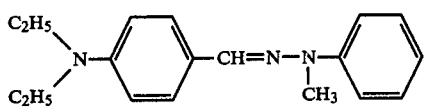

(G) 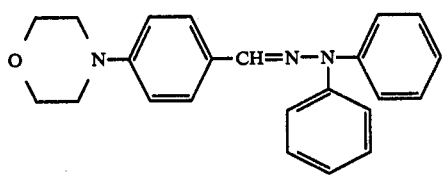

(H) 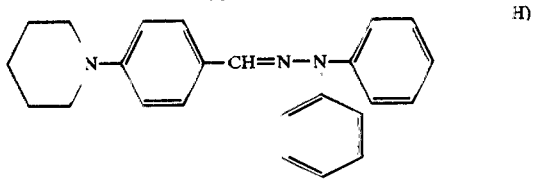

Results thereof are shown in Table 3.

TABLE 3

| Comparative Example No. | Hydrazone compound | $V_0$ (volt) | $V_5$ (volt) | $P_M$ (min.) | E ½ (lux · sec.) |
|---|---|---|---|---|---|
| 1 | (A) | −420 | −340 | 30 | 4.7 |
| 2 | (B) | −360 | −270 | 40 | 5.8 |
| 3 | (C) | −350 | −250 | 40 | 3.0 |
| 4 | (D) | −390 | −260 | 40 | 0.2 |
| 5 | (E) | −340 | −210 | 40 | 3.9 |
| 6 | (F) | −350 | −220 | 40 | 2.5 |
| 7 | (G) | −400 | −300 | 30 | 5.0 |
| 8 | (H) | −420 | −280 | 30 | 4.8 |

EXAMPLES 137-144

Copper phthalocyanine of β-type (1 g) was dispersed in a solution prepared by dissolving 5 g of each hydrazone compound shown in Table 4 and 5 g of a telephthalic acid-isophthalic acid (1:1 in molar ratio) copolyester of bis-phenol A in 150 ml of dichloromethane. Each dispersion was coated on the same casein layer laid on the same aluminum plate as used in Example 1 and dried to form a photosensitive layer of 10 g/m² in coating weight.

Photosensitive members prepared in this way were measured for charge bearing characteristics in the same manner as in Example 1 except that the charging polarity was made positive. Results thereof are shown in Table 4.

TABLE 4

| Example No. | Hydrazone compound | $V_0$ (volt) | $V_5$ (volt) | $P_M$ (min) | E ½ (lux · sec.) |
|---|---|---|---|---|---|
| 137 | No. (2) | +530 | −500 | 4 | 4.8 |
| 138 | No. (33) | +500 | −490 | 3 | 4.8 |
| 139 | No. (59) | +510 | −470 | 5 | 1.1 |
| 140 | No. (85) | +500 | −480 | 3 | 3.1 |
| 141 | No. (134) | +500 | −480 | 4 | 1.8 |
| 142 | No. (154) | +520 | −490 | 4 | 2.7 |
| 143 | No. (183) | +490 | −470 | 2 | 1.4 |
| 144 | No. (219) | +530 | −510 | 4 | 3.7 |

COMPARATIVE EXAMPLES 9-13

Photosensitive members were prepared in the same manner as in Examples 137-144 except for using some of the same hydrazone compounds as used in Comparative Examples 1-8. Results of measuring charge bearing characteristics thereof are shown in Table 5.

TABLE 5

| Comparative Example No. | Hydrazone compound for comparison | $V_0$ (volt) | $V_5$ (volt) | $P_M$ (min.) | E ½ (lux · sec.) |
|---|---|---|---|---|---|
| 9 | (A) | +300 | −210 | 40 | 3.6 |
| 10 | (E) | +330 | −200 | 30 | 1.1 |
| 11 | (D) | +370 | −200 | 40 | 1.8 |
| 12 | (G) | +350 | −230 | 40 | 2.7 |

TABLE 5-continued

| Comparative Example No. | Hydrazone compound for comparison | $V_0$ (volt) | $V_5$ (volt) | $P_M$ (min.) | $E \frac{1}{2}$ (lux · sec.) |
|---|---|---|---|---|---|
| 13 | (B) | +340 | +230 | 40 | 37 |

EXAMPLES 145-152

The following perylene pigment was vacuum-deposited on each of 100-μ aluminum plates to form a charge generation layer 0.15μ thick:

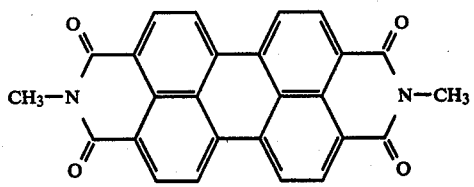

A polyester resin (5 g Vylon 200, mfd. by Toyobo Co., Ltd.), dissolved together with 5 g of each hydrazone compound shown in Table 6 in 150 ml of dichloromethane was coated on each charge generation layer and dried to form a charge transport layer of 11 g/m² in coating weight.

Photosensitive members thus prepared were measured for charge bearing characteristics in the same manner as in Example 1. Results thereof are shown in Table 6.

TABLE 6

| Example No. | Hydrazone compound | $V_0$ (volt) | $V_5$ (volt) | $P_M$ (min) | $E \frac{1}{2}$ (lux · sec) |
|---|---|---|---|---|---|
| 145 | No. (2) | −570 | −560 | 2 | 5.8 |
| 146 | No. (33) | −590 | −570 | 3 | 4.8 |
| 147 | No. (59) | −590 | −580 | 2 | 4.7 |
| 148 | No. (85) | −570 | −550 | 2 | 4.7 |
| 149 | No. (130) | −570 | −490 | 2 | 5.0 |
| 150 | No. (170) | −560 | −550 | 2 | 5.4 |
| 151 | No. (194) | −540 | −530 | 2 | 6.7 |
| 152 | No. (254) | −580 | −570 | 2 | 5.1 |

COMPARATIVE EXAMPLES 14-18

Photosensitive members were prepared and measured for charge bearing characteristics, in the same manner as in Examples 145-152 except for using some of the same hydrazone compounds as used in comparative Examples 1-8. Results thereof are shown in Table 7.

TABLE 7

| Comparative Example No. | Hydrazone compound for comparison | $V_0$ (volt) | $V_5$ (volt) | $P_M$ (min.) | $E \frac{1}{2}$ (lux · sec) |
|---|---|---|---|---|---|
| 14 | (A) | −360 | −240 | 30 | 5.0 |
| 15 | (E) | −340 | −230 | 30 | 18.0 |
| 16 | (D) | −320 | −220 | 20 | 13.6 |
| 17 | (H) | −330 | −220 | 30 | 5.6 |
| 18 | (C) | −390 | −280 | 20 | 11.7 |

EXAMPLES 153-160

Selenium-tellurium (tellurim 10 wt %) was vacuum-deposited on each of aluminum plates to form a charge generation layer 0.8μ thick.

The same solutions as used to form charge transport layers in Examples 1, 20, 38, 51, 63, 81, 95, and 119 were coated individually on the charge generation layers to a dry coating weight of 11 g/m².

Photosensitive members thus prepared were measured for charge bearing characteristics. Results thereof are shown in Table 4.

TABLE 8

| Example No. | Coating liquid charge transport layer | $V_0$ (volt) | $V_5$ (volt) | $P_M$ (min.) | $E \frac{1}{2}$ (lux · sec) |
|---|---|---|---|---|---|
| 153 | The same as in Example 1 | −570 | −560 | 3 | 4.0 |
| 154 | The same as in Example 20 | −570 | −550 | 2 | 4.1 |
| 155 | The same as in Example 38 | −610 | −580 | 3 | 3.6 |
| 156 | The same as in Example 51 | −570 | −550 | 3 | 3.8 |
| 157 | The same as in Example 63 | −600 | −590 | 2 | 3.2 |
| 158 | The same as in Example 81 | −590 | −570 | 2 | 3.3 |
| 159 | The same as in Example 95 | −540 | −530 | 2 | 6.7 |
| 160 | The same as in Example 119 | −580 | −570 | 2 | 3.9 |

EXAMPLE 161

A surface-cleaned molybdenum plate (substrate) 0.2 mm thick was fixed on a prescribed position in a glow discharge chamber for vacuum deposition, which was then evacuated to about $5 \times 10^{-6}$ torr. The temperature of the substrate was raised and settled to 150° C. by regulating a heater. A gas mixture of hydrogen and silane (15 vol% based on hydrogen) was introduced into the chamber and the pressure in the chamber was settled to 0.5 torr by controlling the flow rate of the gas mixture and the main valve of the chamber. Then, 5 MHz high-frequency power was supplied to an induction coil to generate a glow discharge in the inner space, surrounded by the coil, of the chamber, where the input power was regulated to 30 W. Under these conditions, amorphous silicon film was deposited on the substrate to a thickness of 2μ, and then the glow discharge was stopped. The heater and the high-frequency power source were turned off, and after the substrate was cooled to 100° C., the hydrogen and silane inlet valves were closed and the chamber was once evacuated to $10^{-5}$ torr. The chamber pressure was then returned to the atmospheric pressure and the substrate was taken out. In this way, a number of the same substrates were overlaid separately with the same amorphous silicon layers, which in turn were overlaid each with a charge transport layer in the same manner as in Example 1, 20, 38, 51, 63, 81, 95, or 119.

Photosensitive members thus prepared were subjected to corona charging at −6 KV and to image exposure by using a charging-exposing testing machine. The imaging light was projected from a tungsten lamp through a transmission type of test chart. Immediately thereafter, the members were cascaded with positive developer (containing a toner and carrier), forming good toner images.

EXAMPLES 162-168

An aqueous solution of hydroxypropyl cellulose was coated on aluminum plates and dried to form a bond layer of 0.6 g/m² in coating weight on each plate.

A solution was prepared by dissolving 5 g of each hydrazone compound shown in Table 9, 5 g of a poly(N-vinylcarbazole), and 1.0 g of 2,4,7-trinitrofluorenone in 150 ml of dichoromethane, and 1.0 g of the same disazo pigment as used in Example 1 was dispersed in the solution. The dispersion thus prepared was coated on the bond layer and dried to form a photosensitive layer of 11 g/m² in coating weight.

Photosensitive members prepared in this way were measured for charge bearing characteristics in the same manner as in Example 1 except that the charging polarity was made positive. Results thereof are shown in Table 9.

TABLE 9

| Example No. | Hydrazone compound | $V_0$ (volt) | $V_5$ (volt) | $P_M$ (min.) | $E\frac{1}{2}$ (lux · sec.) |
|---|---|---|---|---|---|
| 162 | No. (2) | +540 | +520 | 3 | 12.0 |
| 163 | No. (33) | +530 | +510 | 2 | 11.4 |
| 164 | No. (85) | +520 | +490 | 3 | 12.9 |
| 165 | No. (111) | +520 | +500 | 3 | 12.8 |
| 166 | No. (150) | +510 | +480 | 3 | 13.7 |
| 167 | No. (183) | +530 | +500 | 3 | 13.0 |
| 168 | No. (219) | +500 | +490 | 2 | 14.0 |

EXAMPLE 169

The same bond layer-coated aluminum plate as of Example 162 was prepared.

A dispersion of 1.0 g of a disazo pigment of the formula

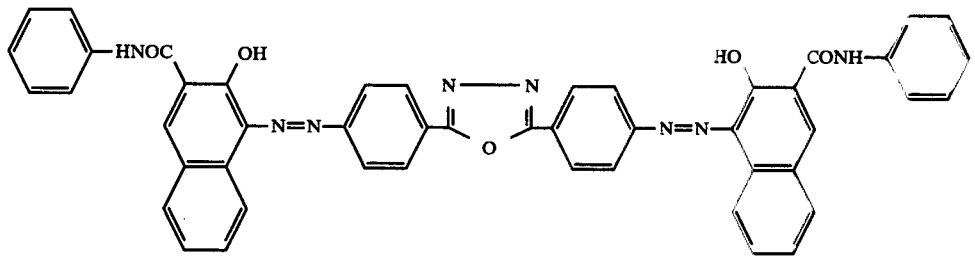

in a solution of 5 g of hydrazone compound No. 59 cited above, 5 g of a poly(N-vinylcarbazole), and 0.1 g of 2,4,7-trinitrofluorenone in 150 ml of dichloromethane was coated on the bond layer and dried to form a photosensitive layer of 11 g/m² in coating weight.

The photosensitive member thus prepared was measured for charge bearing characteristics in the same manner as in Example 1 except that the charging polarity was made positive. Results thereof are shown in Table 10

TABLE 10

| | |
|---|---|
| $V_0$ | +500 volt |
| $V_5$ | +480 volt |
| $P_M$ | 4 minutes |
| $E\frac{1}{2}$ | 12.4 lux · sec. |

What we claim is:

1. An electrophotographic photosensitive member comprising a conductive substrate and a layer containing at least one hydrazone compound represented by the following formula (1), (2), (3), (4), or (5) and a binder:

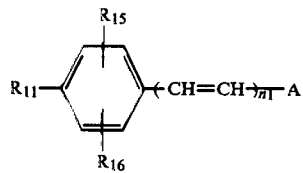

Formula (1)

in Formula (1); $R_{11}$ represents alkoxy or disubstituted amino; $R_{15}$ and $R_{16}$ represent hydrogen, halogen, or an organic monovalent residue; $n_1$ is 0 or 1; and A represents

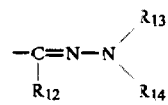

wherein $R_{12}$, $R_{13}$, and $R_{14}$ represent alkyl, aryl, or aralkyl, substituted or unsubstituted, with the proviso, that;

when $R_{12}$ is alkyl, $R_{13}$ represents aryl and $R_{14}$ represents alkyl, aryl, or aralkyl, when $R_{12}$ is aryl, $R_{13}$ represents aralkyl and $R_{14}$ represents aryl, and when $R_{12}$ is aralkyl, $R_{13}$ and $R_{14}$ represent alkyl, aryl, or aralkyl, Formula (2)

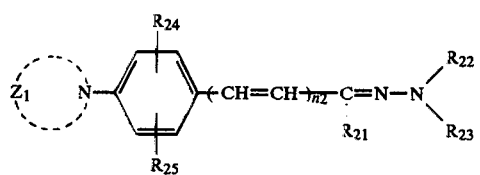

in Formula (2); $Z_1$ represents a residue necessary to complete a cyclic amino group; $R_{21}$, $R_{22}$, and $R_{23}$ represent alkyl, aryl, or aralkyl, substituted or unsubstituted; $R_{24}$ and $R_{25}$ represent hydrogen, halogen, or an organic monovalent residue; and $n_2$ is 0 or 1, Formula (3)

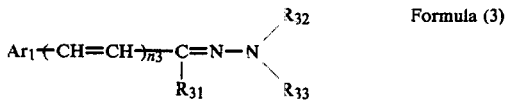

in Formula (3); $Ar_1$ represents a substituted or unsubstituted aromatic polycyclic residue; $R_{31}$, $R_{32}$, and $R_{33}$ represent alkyl, aryl, or aralkyl, substituted or unsubstituted; and $n_3$ is 0 or 1,

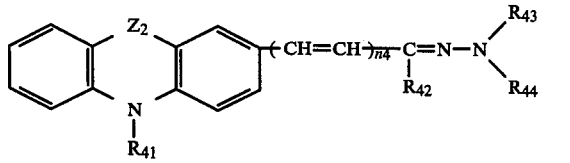

Formula (4)

in Formula (4); $Z_2$ represents oxygen, sulfure, or —$CH_2$—; $R_{41}$ represents alkyl or aralkyl, substituted or unsubstituted; $R_{42}$, $R_{43}$, and $R_{44}$ represent alkyl, aryl, or aralkyl, substituted or unsubstituted; and $n_4$ is 0 or 1,

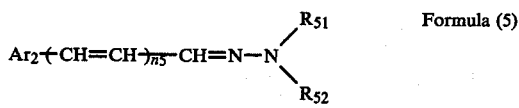

Formula (5)

in Formula (5); $Ar_2$ represents a substituted or unsubstituted aromatic polycyclic residue or a phenyl substituted at least by piperidino or morpholine; $R_{51}$ represents substituted or unsubstituted naphthyl; $R_{52}$ represents alkyl, aryl, or aralkyl, substituted or unsubstituted; and $n_5$ is 0 or 1.

2. An electrophotographic photosensitive member of claim 1, wherein $R_{11}$ in Formula (1) is dialkylamino.

3. An electrophotographic photosensitive member of claim 2, wherein $R_{11}$ in Formula (1) is dimethylamino, diethylamino, dipropylamino, or dibutylamino.

4. An electrophotographic photosensitive member of claim 1, where in Formula (1), when $R_{12}$ is substituted or unsubstituted alkyl, $R_{13}$ is $\alpha$-naphthyl or $\beta$-naphthyl.

5. An electrophotographic photosensitive member of claim 1, wherein $n_1$ in Formula (1) is zero.

6. An electrophotographic photosensitive member of claim 1, wherein $n_2$ in Formula (2) is zero.

7. An electrophotographic photosensitive member of claim 1, wherein $Z_1$ in Formula (2) is a residue necessary to complete piperidino, 1-pyrrolidinyl, or morpholino.

8. An electrophotographic photosensitive member of claim 1, wherein $Ar_1$ in Formula (3) is naphthyl, anthryl, or pyrenyl.

9. An electrophotographic photosensitive member of claim 1, wherein $n_3$ in Formula (3) is zero.

10. An electrophotographic photosensitive member of claim 1, wherein $n_4$ in Formula (4) is zero.

11. An electrophotographic photosensitive member of claim 1, wherein $Ar_2$ in Formula (5) is naphthyl, anthryl, or pyrenyl.

12. An electrophotographic photosensitive member of claim 1, wherein $n_5$ in Formula (5) is zero.

13. An electrophotographic photosensitive member of claim 1, wherein the layer containing at least one hydrazone compound represented by Formula (1), (2), (3), (4), or (5) and a binder is a charge transport layer.

14. An electrophotographic photosensitive member of claim 13, which has both a charge generation layer and a charge transport layer on conductive substrate thereof.

15. An electrophotographic photosensitive member of claim 14, wherein the charge transport layer is formed on the upper side of the charge generation layer.

16. An electrophotographic photosensitive member of claim 15, which has a bond layer between the conductive substrate and the charge generation layer.

17. An electrophotographic photosensitive member of claim 13, wherein the charge generation layer contains at least one charge-generating substance selected from the group consisting of selenium, selenium-tellurium, selenium-arsenic, cadmium sulfide, amorphous silicon, pyrylium dyes, thiopyrylium dyes, triarylmethane dyes, thiazine dyes, cyanine dyes, phthalocyanine pigments, perylene pigments, indigo pigments, thioindigo pigments, quinacridone pigments, squaric acid pigments, azo pigments, and polycyclic quinone pigments.

18. An electrophotographic photosensitive member of claim 17, wherein the charge generation layer comprises a binder and at least one charge-generating substance selected from the group consisting of pyrylium dyes, thiopyrylium dyes, triarylmethane dyes, thiazine dyes, cyanine dyes, phthalocyanine pigments, indigo pigments, thioindigo pigments, quinacridone pigments, squaric acid pigments, azo pigments, and polycyclic quinone pigments.

19. An electrophotographic photosensitive member of claim 18, wherein said azo pigments are disazo pigments.

20. An electrophotographic photosensitive member of claim 18, wherein the phthalocyanine pigment is copper phthalocyanine.

21. An electrophotographic photosensitive member of claim 17, wherein the charge generation layer is formed of amorphous silicon.

22. An electrophotographic photosensitive member of claim 17, wherein the charge generation layer is formed from the vacuum-deposited perylene pigment.

23. An electrophotographic photosensitive member of claim 17, wherein the charge generation layer is formed from vacuum-deposited selenium-tellurium.

24. An electrophotographic photosensitive member of claim 1, wherein said layer, containing a binder and at least one hydrazone compound represented by Formula (1), (2), (3), (4), or (5), also contains at least one pigment or dye selected from the group consisting of cadmium sulfide, pyrylium dyes, thiopyrylium dyes, triarylmethane dyes, thiazine dyes, cyanine dyes, phthalocyanine pigments, perylene pigments, indigo pigments, thioindigo pigments, quinacridone pigments, squaric acid pigments, azo pigments, and polycyclic quinone pigments.

25. An electrophotographic photosensitive member of claim 24, wherein said layer, containing a binder and at least one hydrazone compound represented by Formula (1), (2), (3), (4), or (5), also contains a photoconductive polymer and at least one pigment or dye selected from the group consisting of cadmium sulfide, pyrylium dyes, thiopyrylium dyes, triarylmethane dyes, thiazine dyes, cyanine dyes, phthalocyanine pigments, perylene pigments, indigo pigments, thioindigo pigments, quinacridone pigments, squaric acid pigments, azo pigments, and polycyclic quinone pigments.

26. An electrophotographic photosensitive member of claim 25, wherein said photoconductive polymer is poly(N-vinylcarbazole).

* * * * *

UNITED STATES PATENT AND TRADEMARK OFFICE
CERTIFICATE OF CORRECTION

PATENT NO. : 4,456,671

DATED : June 26, 1984

INVENTOR(S) : MABUCHI, ET AL

It is certified that error appears in the above-identified patent and that said Letters Patent is hereby corrected as shown below:

Col. 1, line 45, insert --being-- before "lightweight"

Col. 3, line 54, change "diporpylamino" to --dipropylamino--

Col. 6, line 13, change "aromiatic" to --aromatic--
       line 27, change "alkoxy" to --alkoxys--

Col. 7, form (7), attached illustration is correct.

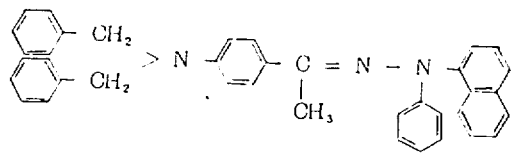

Col. 47, line 11, change dinitrosalicyclic    to
                 --dinitrosaliscylic--

UNITED STATES PATENT AND TRADEMARK OFFICE
CERTIFICATE OF CORRECTION

PATENT NO. : 4,456,671
DATED : June 26, 1984
INVENTOR(S) : MABUCHI, ET AL

It is certified that error appears in the above-identified patent and that said Letters Patent is hereby corrected as shown below:

Col. 55, form (42) attached illustration is correct (42)

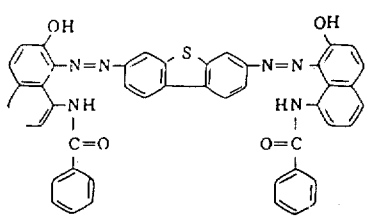

Col. 59, form (50) attached illustration is correct (50)

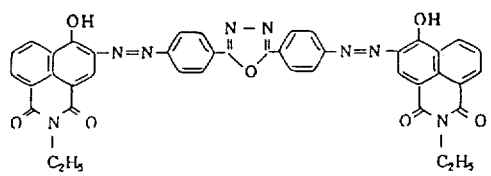

UNITED STATES PATENT AND TRADEMARK OFFICE
CERTIFICATE OF CORRECTION

PATENT NO. : 4,456,671

DATED : June 26, 1984

INVENTOR(S) : MABUCHI, ET AL

It is certified that error appears in the above-identified patent and that said Letters Patent is hereby corrected as shown below:

Col. 59, form (51) attached illustration is correct (51)

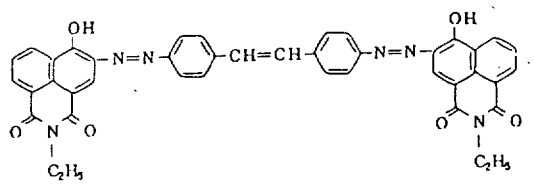

Col. 59, form (52) attached illustration is correct (52)

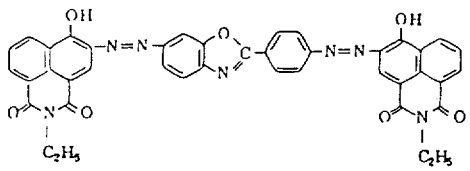

UNITED STATES PATENT AND TRADEMARK OFFICE
CERTIFICATE OF CORRECTION

PATENT NO. : 4,456,671

DATED : June 26, 1984

INVENTOR(S) : MABUCHI, ET AL

It is certified that error appears in the above-identified patent and that said Letters Patent is hereby corrected as shown below:

Col. 59, form (53) attached illustration is correct

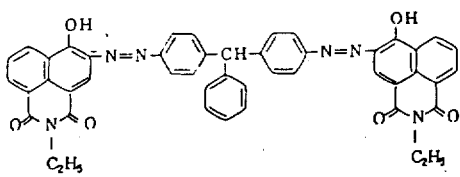

(53)

Col. 63, line 10, insert --from-- following "ranges"
line 46, insert --at-- following "arrive"

Col. 64, line 68, change "exposured" to --exposed--

Col. 65, line 10, change "Examples 2-135" to --Examples 2-136--.

Col. 70, line 7, change "Table 4" to --Table 8--.

UNITED STATES PATENT AND TRADEMARK OFFICE
CERTIFICATE OF CORRECTION

PATENT NO. : 4,456,671

DATED : June 26, 1984

INVENTOR(S) : MABUSHI, ET AL

It is certified that error appears in the above-identified patent and that said Letters Patent is hereby corrected as shown below:

Col. 71, line 3, change "1.0g" to --0.1g--.

Col. 73, line 11, change "sulfure" to --sulfur--.

Signed and Sealed this

Ninth Day of July 1985

[SEAL]

Attest:

DONALD J. QUIGG

Attesting Officer        Acting Commissioner of Patents and Trademarks